(12) United States Patent
Ahn et al.

(10) Patent No.: US 10,562,841 B2
(45) Date of Patent: Feb. 18, 2020

(54) PROCESS FOR CATALYTIC HYDROGENATION OF HALONITROAROMATICS

(71) Applicant: Monsanto Technology LLC, St. Louis, MO (US)

(72) Inventors: John H. Ahn, Town and Country, MO (US); Kam-To Wan, Town and Country, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/761,986

(22) PCT Filed: Sep. 30, 2016

(86) PCT No.: PCT/US2016/054659
§ 371 (c)(1),
(2) Date: Mar. 21, 2018

(87) PCT Pub. No.: WO2017/059192
PCT Pub. Date: Apr. 6, 2017

(65) Prior Publication Data
US 2018/0282258 A1 Oct. 4, 2018

Related U.S. Application Data

(60) Provisional application No. 62/236,026, filed on Oct. 1, 2015, provisional application No. 62/236,010, filed on Oct. 1, 2015.

(51) Int. Cl.
*C07C 209/36* (2006.01)
*B01J 21/18* (2006.01)
*B01J 23/42* (2006.01)
*C07C 231/02* (2006.01)

(52) U.S. Cl.
CPC ........... *C07C 209/365* (2013.01); *B01J 21/18* (2013.01); *B01J 23/42* (2013.01); *C07C 231/02* (2013.01)

(58) Field of Classification Search
None
See application file for complete search history.

(56) References Cited

U.S. PATENT DOCUMENTS

| | | | |
|---|---|---|---|
| 1,456,969 A | 5/1923 | Brown et al. |
| 2,765,345 A | 10/1956 | Spiegler |
| 2,823,235 A | 2/1958 | Graham et al. |
| 3,073,865 A | 1/1963 | Spiegler |
| 3,145,231 A | 8/1964 | Kosak |
| 3,291,832 A | 12/1966 | Kosak |
| 3,474,144 A | 10/1969 | Winfred et al. |
| 4,020,107 A | 4/1977 | Kosak |
| 4,161,611 A | 7/1979 | Kim |
| 4,760,187 A | 7/1988 | Kosak |
| 5,068,436 A | 11/1991 | May |
| 5,512,529 A | 4/1996 | Deller et al. |
| 6,197,716 B1 | 3/2001 | Baumeister et al. |
| 6,417,133 B1 | 7/2002 | Ebner et al. |
| 6,586,621 B2 | 7/2003 | Leiber et al. |
| 8,703,639 B2 | 4/2014 | Wan et al. |
| 2009/0131727 A1 | 5/2009 | Yang et al. |
| 2013/0245335 A1 | 9/2013 | Zhou et al. |

FOREIGN PATENT DOCUMENTS

| | | |
|---|---|---|
| CN | 1235888 C | 1/2006 |
| CN | 101049562 A | 10/2007 |
| CN | 100441293 C | 12/2008 |
| CN | 101735073 A | 7/2010 |
| CN | 101811973 A | 8/2012 |
| CN | 103113233 A | 5/2013 |
| CN | 103191730 A | 7/2013 |
| CN | 103333075 A | 10/2013 |
| CN | 103467307 A | 12/2013 |
| CN | 103467308 A | 12/2013 |
| EP | 0073105 A1 | 3/1983 |
| JP | 2004277409 A | 10/2004 |
| WO | 2015011716 A1 | 1/2014 |
| WO | 2015095284 A1 | 6/2015 |

OTHER PUBLICATIONS

Ichikawa, S., et al., "Chemoselective Hydrogenation of Halonitroaromatics over Platinum on Carbon as Catalyst in Supercritical Carbon Dioxide," 2014, Adv Synth & Cataly, 356/11-12:2643-2652, 10 pages.
Beswick, O., et al., "Iron Oxide Nanoparticles Supported on Activated Carbon Fibers Catalyze Chemoselective Reduction of Nitroarenes Under Mild Conditions," 2015, Catalysis Today, 249:45-51, Abstract Only.
Chandrappa, S., et al., "An Efficient Method for Aryl Nitro Reduction and Cleavage of Azo Compounds Using Iron Powder/Calcium Chloride," 2010, Synlett, 20:3019-3022, Abstract only.
Dovell, F.S., et al., "Platinum Metal Sulfides as Heterogenous Hydrogenation Catalysts," 1965, J Am Chem Soc, 87/12:2767-2768. First Page Only.
Farhadi, S., et al., "Microwave-Assisted Rapid and Efficient Reduction of Aromatic Nitro Compounds to Amines with Propan-2-ol Over Nanosized Perovskite-Type SmFeO3 Powder as a New Recyclable Heterogeneous Catalyst," 2011, J Chem Res, 35/2:104-108, Abstract only.

(Continued)

*Primary Examiner* — Sudhakar Katakam
*Assistant Examiner* — Jennifer C Sawyer
(74) *Attorney, Agent, or Firm* — Stinson LLP; Eric C. Robert

(57) ABSTRACT

The present invention generally relates to processes for the catalytic hydrogenation of halonitroaromatics. In particular, the present invention includes processes for the catalytic hydrogenation of halonitroaromatics such as 2,5-dicloronitrobenzene to 2,5-dichloroaniline over a platinum-containing catalyst. The present invention also relates to processes for producing 3,6-dichloro-2-methoxybenzoic acid.

34 Claims, 15 Drawing Sheets

(56) References Cited

OTHER PUBLICATIONS

Farhadi, S., et al., "NiO Nanoparticles Prepared via Thermal Decomposition of the Bis(Dimethylglyoximato)Nickel(II) Complex: A Novel Reusable Heterogeneous Catalyst for Fast and Efficient Microwave-Assisted Reduction of Nitroarenes with Ethanol," 2011, Polyhedron, 30/4:606-613, Abstract only.

Ferrier, G.G., et al., "A New Platinum Catalysts for the Hydrogenation of Halonitroaromatics," 1983, Platinum Metals Rev., 27/2:72-77, 6 pages.

Gawande, M.B., et al., "First Application of Core-Shell AG@Ni Magnetic Nanocatalyst for Transfer Hydrogenation Reactions of Aromatic Nitro and Carbonyl Compounds," 2013, RCS Advances, 3:1050-1054, 5 pages.

Gawande, M.B., et al., "Regio-and Chemoselective Reduction of Nitroarenes and Carbonyl Compounds over Recyclable Magnetic Ferrite-Nickel Nanoparticles (Fe3O4—Ni) by Using Glycerol as a Hydrogen Source," 2012, Chem Eur J, 18:12628-12632, 5 pages.

Goyal, A., et al., "CoMn0.2Fe1.8O4 Ferrite Nanoparticles Engineered by Sol-Gel Technology: an Expert and Versatile Catalyst for the Reduction of Nitroaromatic Compounds," J Mat Chem A, 2014, 2/44:18848-18860, Abstract Only.

Greenfield, H., et al., "Metal Sulfide Catalysts for Hydrogenation of Halonitrobenzenes to Haloanilines," 1967, J Org Chem, 32/11:3670-3671, First page only.

He, D., et al., "Synthesis of Chloroanilines: Selective Hydrogenation of the Nitro in Chloronitrobenzenes Over Zirconia-Supported Gold Catalyst," 2007, Green Chemistry, 9/8:849-851.

Ichikawa, S., et al., "Chemoselective Hydrogenation of Halonitroaromatics over Platinum on Carbon as Catalyst in Supercritical Carbon Dioxide," 2014, Adv Synth & Cataly, 356/11-12:2643-2652, Abstract only.

Kosak, J.R., Ph.D., "Catalytic Hydrogenation of Aromatic Halonitro Compounds," 1970, Annals New York Academy of Sciences, 175-185, 11 pages.

Kosak, J.R., "Hydrogenation of Haloaromatic Nitro Compounds," 1980, Catalysis in Organic Synthesis, W.H. Jones, Editor, Academic Press, Inc., 107-117, 8 pages.

Kumar, K.A., et al., "Chemoselective Hydrogenation of Aromatic Nitro Compounds Using Diammonium Hydrogen Phosphite and Commercial Zinc Dust," 2008, E-Journal of Chemistry, 5/4:914-917, 4 pages.

Lara, P. et al., "The Hydrogenation of Nitroarenes Mediated by Platinum Nanoparticles: an Overview," 2014, Catal Sci Technol, 4:2445-2465, 21 pages.

Lin, P-H, et al., "Synthesis of Chlorinated and Non-Chlorinated Biphenyl-2,3- and 3,4-Catechols and Their [2H3]—Isotopomers," 2004, Organic & Biomolecular Chemistry, 2/18:2624-2629, Abstract only.

Long, Y., et al., "Distinctive Size Effects of Pt Nanoparticles Immobilized on Fe3O4@PPy Used as an Efficient Recyclable Catalyst for Benzylic Alcohol Aerobic Oxidation and Hydrogenation Reduction of Nitroaromatics," 2015, New J of Chem, 39/2:1179-1185, Abstract only.

Meng, M-Y., et al., "Study on the Preparation of Halogenated Aromatic Amines by Catalytic Hydrogenation," 2006, Fine and Specialty Chemicals, 14/14:26-23, Abstract Only.

Pandarus, V., et al., "Selective Hydrogenation of Functionalized Nitroarenes under Mild Conditions," 2011, Catalysis Science & Technology, 1:1616-1623, 8 Pages.

Pandarus, V., et al., "A New Class of Heterogeneous Platinum Catalysts for the Chemoselective Hydrogenation of Nitroarenes," 2011, Adv Synth & Catal, 353/8:1306-1316, 11 pages.

Shil, A.K., et al., "Solid Supported Platinum(0) Nanoparticles Catalyzed Chemo-Selective Reduction of Nitroarenes to N-arylhydroxylamines," 2013, Green Chem, 15:3421-3428, Abstract Only.

Smith, G.V., et al., "Hydrogenation and Dehydrohalogenation of p-Chloronitrobenzene: Effect of Pd Metal particle Size on Activity and Selectivity," 1994, Catalysis of Organic Reactions, 469-474, 6 pages.

Sun, Y., et al., "Catalytic Hydrogenation of Chloronitrobenzenes to Prepare Chloroanilines Over Water-Soluble Nickel Nanoparticle," 2007, Chinese J App Chem, 24/4:483-485, Abstract Only.

Witte, P.T., et al., "BASF NanoSelect™ Technology: Innovative Supported Pd- and Pt-based Catalysts for Selective hydrogenation Reactions," 2012, Top Catal, 55:505-511, 7 pages.

Wu, G., et al., "Novel ZnX2-Modulated Pd/C and Pt/C Catalysts for Chemoselective Hydrogenation and Hydrogenolysis of Halogen-Substituted Nitroarenes, Alkenes, Benzyl Ethers, and Aromatic Ketones," 2003, Synthesis, 11:1657-1660. First Page Only.

Xiao, C., et al., "Selective Hydrogenation of Halonitrobenzenes," 2012, Curr Org Chem, 16:280-296, 17 pages.

Zhou, H., et al., "A Study on Catalytic Hydrogenation for Preparation of 2,5-Dichloroaniline," 2002, Dyestuff Industry, 39/2:32-33, Abstract Only.

US 10,562,841 B2

PROCESS FOR CATALYTIC HYDROGENATION OF HALONITROAROMATICS

REFERENCE TO RELATED APPLICATIONS

This application is the 371 National Stage Application of International Application Serial. No. PCT/US2016/054659, filed Sep. 30, 2016, and claims the benefit of U.S. Provisional Application Ser. No. 62/236,010, filed Oct. 1, 2015, the contents of each of which are incorporated herein by reference.

FIELD OF THE INVENTION

The present invention generally relates to processes for the catalytic hydrogenation of halonitroaromatics. In particular, the present invention includes processes for the catalytic hydrogenation of halonitroaromatics such as 2,5-dicloronitrobenzene to 2,5-dichloroaniline over a platinum-containing catalyst. The present invention also relates to processes for producing 3,6-dichloro-2-methoxybenzoic acid (dicamba).

BACKGROUND OF THE INVENTION

Halonitroaromatic compounds include various mono- and di-halo substituted nitroaromatics. Specific examples include chloronitroaromatic compounds such as 2-, 3-, and 4-chloronitrobenzene; 2,4-dicloronitrobenzene; 2,5-dicloronitrobenzene; 3,4-dichloronitrobenzene, among others. The catalytic hydrogenation of halonitroaromatics is a reaction of significant industrial importance because the resulting haloaminoaromatic compounds (e.g., haloanilines) are useful as intermediates in the production of certain agrochemicals, pharmaceuticals, and polymers. For example, 2,5-dichloroaniline can be used as an intermediate in the production of 3,6-dichloro-2-methoxybenzoic acid (also known by its common name dicamba), which is a highly effective and commercially important herbicide that is useful for controlling a wide variety of unwanted vegetation, including agricultural weeds. Convenient and economical methods of preparing dicamba, therefore, are of significant commercial importance.

Various processes for the catalytic hydrogenation of halo-nitroaromatics are described in references such as U.S. Pat. Nos. 3,073,865; 3,145,231; 3,291,832; 4,020,107; 4,760,187; as well as Kosak, "Hydrogenation of Haloaromatic Nitro Compounds," Catalysis in Organic Synthesis, Academic Press, London, 1980, 107-117. One problem typically encountered during the hydrogenation process is the loss of selectivity to the desired haloaminoaromatic product through dehalogenation of the haloaminoaromatic product. Attempts to solve this problem have focused on introducing catalyst modifiers or additives into the reaction medium to suppress the dehalogenation reaction. For example, U.S. Pat. No. 3,073,865 describes the addition of a hydroxide or oxide of magnesium to the reaction medium as a dehalogenation suppressor. U.S. Pat. No. 3,145,231 discloses the use of cycloaliphatic amines such piperazine and morpholine as dehalogenation suppressors. U.S. Pat. No. 4,020,107 introduces an acidic phosphorous compound to suppress the dehalogenation reaction. U.S. Pat. No. 4,760,187 uses a ruthenium-platinum catalyst for halogenating chloronitrobenzenes to chloroanilines that also reduces dehalogenation. Also, Kosak teaches that the use of a sulfided platinum catalyst is one of the more effective procedures for minimizing dehalogenation.

Although these processes may be effective strategies for minimizing dehalogenation of the halonitroaromatic compound, these processes introduce additional components to the reaction medium or catalyst material. In multi-step processes that include the step of hydrogenating a halonitroaromatic, introducing additional components to the reaction mixture can affect downstream processes and reactions and may necessitate further separation operations, which increase process costs. Also, introducing catalyst modifiers can increase process costs and result in the presence of undesired metal contaminants or the production of other undesired reaction products.

Accordingly, there remains a need for processes for the catalytic hydrogenation of halonitroaromatic compounds that minimize the introduction of extraneous additives and catalyst modifiers but still provide for high selectivity to the haloaminoaromatic product and limit selectivity loss through dehalogenation.

SUMMARY OF THE INVENTION

The present invention is generally directed to processes for the catalytic hydrogenation of halonitroaromatics to haloaminoaromatics. For example, the present invention includes processes for the catalytic hydrogenation of halo-nitroaromatics such as 2,5-dicloronitrobenzene to 2,5-dichloroaniline in the presence of a platinum-containing catalyst. The present invention also includes processes for producing 3,6-dichloro-2-methoxybenzoic acid (dicamba) using 2,5-dichloroaniline produced in accordance with the present invention.

Aspects of the present invention are directed to processes for the hydrogenation of halonitroaromatic compounds using catalysts that have improved selectivity for the production of haloaminoaromatics. In particular, various processes of the present invention provide for a reduction in the loss of selectivity to dechlorination (i.e., suppress dehalogenation). Processes in accordance with the present invention with improved selectivity for haloaminoaromatics significantly improve process economics.

Further aspects of the present invention are directed to processes that minimize or eliminate the addition of extraneous additives to the hydrogenation reaction medium and catalyst while maintaining a high selectivity for the haloaminoaromatic product. Advantageously, minimizing or eliminating extraneous additives reduces or avoids the need for subsequent processes, such as additional separation processes, to manage these additives, which improves process economics.

Other aspects of the present invention are directed to processes of using catalysts which are more stable under various conditions of the hydrogenation reaction (e.g., more resistant to leaching in an acidic solvent). For example, reduced leaching of platinum from the catalyst increases its useful life and reduces process costs associated with platinum loss and recovery of platinum from the reaction product.

Still further aspects of the present invention are directed to processes for preparing 3,6-dichloro-2-methoxybenzoic acid using 2,5-dichloroaniline obtained from the hydrogenation processes described herein as an intermediate.

In various embodiments, the present invention is directed to a process for preparing a haloaminoaromatic compound comprising: feeding hydrogen and a feed mixture comprising a halonitroaromatic compound to a hydrogenation zone; and reacting the halonitroaromatic compound with hydrogen in the presence of a hydrogenation catalyst comprising platinum on a carbon support to produce a reaction product comprising the haloaminoaromatic compound, wherein the process further comprises one or more of the following features:
(1) the hydrogenation catalyst is a calcined hydrogenation catalyst;
(2) the feed mixture further comprises a solvent comprising an acid;
(3) the hydrogenation catalyst is an unmodified hydrogenation catalyst;
(4) the feed mixture is free of dehalogenation suppressors;
(5) the reaction product further comprises 2-chloroaniline and 3-chloroaniline and the mole ratio of 3-chloroaniline to 2-chloroaniline is no greater than about 6:1, no greater than about 5:1, no greater than about 4:1, no greater than about 3:1, no greater than about 2:1, or no greater than about 1:1;
(6) the reaction product further comprises 2-chloroaniline and 3-chloroaniline, and the loss of selectivity from 2,5-dichloroaniline to 2-chloroaniline and 3-chloroaniline is less than about 0.4 mol. %, less than about 0.3 mol. %, or less than about 0.2 mol. %; and/or
(7) the hydrogenation catalyst comprises platinum metal particles of a size up to 10 nm in their largest dimension and no more than about 50% (number basis), no more than about 25% (number basis), no more than about 20% (number basis), no more than about 15% (number basis), or no more than about 10% (number basis) of the platinum metal particles are less than 2 nm in their largest dimension.

In further embodiments, the present invention is directed to a process for producing 2,5-dichloroaniline comprising: feeding hydrogen and a feed mixture comprising 2,5-dichloronitrobenzene and a solvent comprising an acid to a hydrogenation zone; and reacting the 2,5-dichloronitrobenzene with hydrogen in the presence of a heterogeneous hydrogenation catalyst comprising platinum on a carbon support to produce a reaction product comprising 2,5-dichloroaniline.

Other embodiments of the present invention include a process for producing 2,5-dichloroaniline comprising: feeding hydrogen and a feed mixture comprising 2,5-dichloronitrobenzene to a hydrogenation zone; and reacting the 2,5-dichloronitrobenzene with hydrogen in the presence of a heterogeneous hydrogenation catalyst comprising platinum on a carbon support to produce a reaction product comprising 2,5-dichloroaniline, wherein the hydrogenation catalyst is an unmodified hydrogenation catalyst and the feed mixture is free of dehalogenation suppressors.

Still further embodiments of the present invention include a process for producing 2,5-dichloroaniline comprising: feeding hydrogen and a feed mixture comprising 2,5-dichloronitrobenzene to a hydrogenation zone; and reacting the 2,5-dichloronitrobenzene with hydrogen in the presence of a heterogeneous hydrogenation catalyst comprising platinum on a carbon support to produce a reaction product comprising 2,5-dichloroaniline, wherein the hydrogenation catalyst is a calcined hydrogenation catalyst.

Other objects and features will be in part apparent and in part pointed out hereinafter.

DESCRIPTION OF THE PREFERRED EMBODIMENTS

Figure 1:
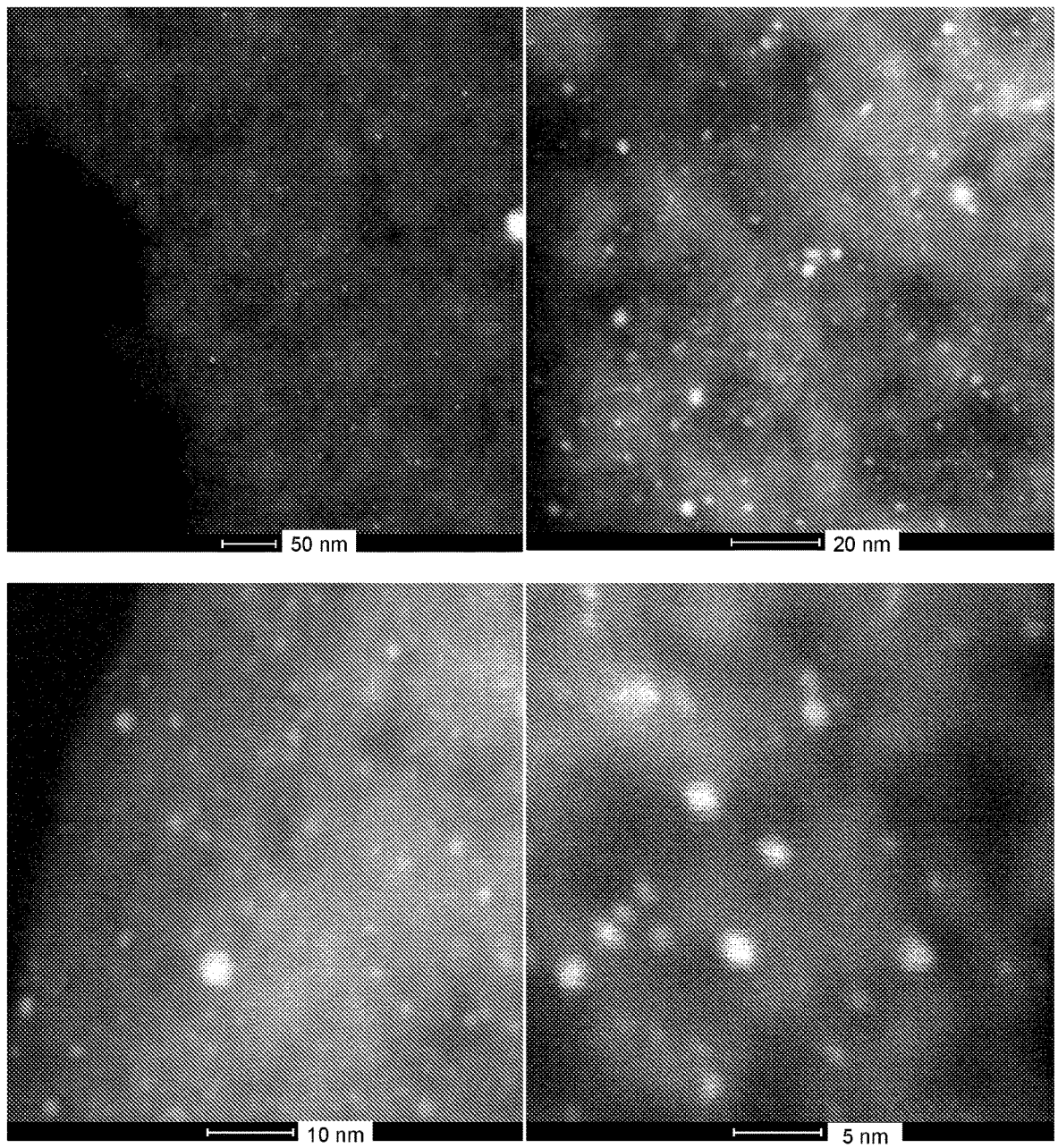
FIG. 1 presents a series of scanning transmission electron microscopy (STEM) images of the surface of a commercial platinum on carbon catalyst prior to calcination.

Various processes in accordance with the present invention for the production of a haloaminoaromatic compound generally include catalytically reducing a halonitroaromatic compound with hydrogen in the presence a hydrogenation catalyst. In particular, processes in accordance with various aspects of the present invention comprise feeding hydrogen and a feed mixture comprising a halonitroaromatic compound to a hydrogenation zone and reacting the halonitroaromatic compound with hydrogen in the presence of a hydrogenation catalyst to produce a reaction product comprising a haloaminoaromatic compound. Generally, the hydrogenation catalyst is heterogeneous and comprises noble metal (e.g., platinum) particles on a carbon support. Noble metals include platinum, palladium, ruthenium, rhodium, iridium, silver, osmium, and gold. Platinum is a preferred noble metal. The reaction scheme for the hydrogenation of a halonitrobenzene compound with hydrogen gas to a haloaniline is as follows:

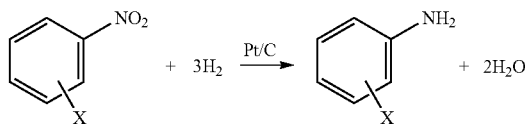

where X is one or more halo substituents (e.g., 1, 2, or 3) such as fluoro, chloro, bromo, or iodo.

The processes of the present invention can be used for the conversion of various halonitroaromatic compounds. For example, the halonitroaromatic compound can be a halonitrobenzene compound (e.g., 2-, 3-, 4-chloronitrobenzene). The halonitroaromatic compounds can have one, two, or more halo substituents. In various embodiments, the halonitroaromatic compounds comprise dihalo-substituted nitrobenzenes, such as dichloronitrobenzenes. Specific examples of dichloronitrobenzenes include 2,4-dicloronitrobenzene; 2,5-dicloronitrobenzene; 3,4-dichloronitrobenzene; and 3,5-dichloronitrobenzene.

One preferred halonitroaromatic compound comprises 2,5-dicloronitrobenzene, which is a useful intermediate in the production of 3,6-dichloro-2-methoxybenzoic acid (dicamba). Accordingly, various processes of the present invention are directed to hydrogenation of 2,5-dichloronitrobenzene to 2,5-dichloroaniline, which is shown in the reaction scheme below. The processes generally comprise feeding hydrogen and a feed mixture comprising 2,5-dichloronitrobenzene to a hydrogenation zone; and reacting the 2,5-dichloronitrobenzene with hydrogen in the presence of a heterogeneous hydrogenation catalyst comprising platinum on a carbon support to produce a reaction product comprising 2,5-dichloroaniline.

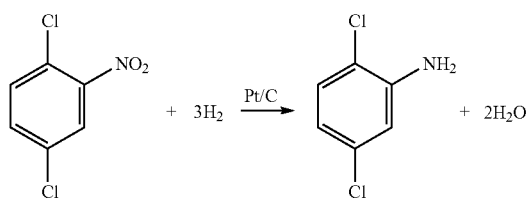 [SMILES: O=[N+]([O-])c1cc(Cl)ccc1Cl ; Nc1cc(Cl)ccc1Cl]

The halogenation reaction is nearly quantitative in that the yield of 2,5-dichloroaniline is at least about 90%, at least about 92%, at least about 95%, at least about 98%, or at least about 99%. However, as noted, the 2,5-dichloroaniline product can be further reduced resulting in dehalogenated compounds such as 2- and 3-chloroaniline. The dehalogenation reaction can proceed as follows:

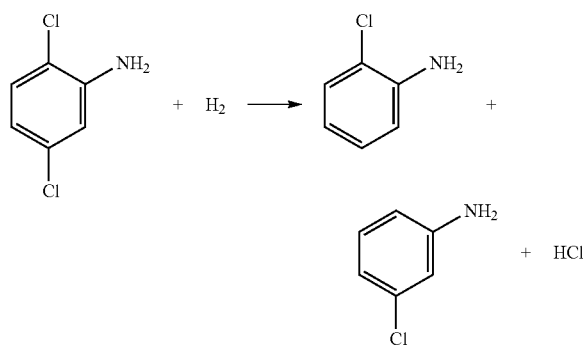

The dehalogenation reaction results in a loss of selectivity to the 2,5-dichloroaniline product.

Applicants have discovered that the loss of selectivity resulting from the dehalogenation of the haloaminoaromatic product (e.g., 2,5-dichloroaniline) can be reduced by controlling or adjusting the platinum particle size distribution on the hydrogenation catalyst. Without being bound by theory, applicants believe that the dehalogenation reaction is dependent at least in part on the platinum particle sizes on the carbon support of the catalyst. The presence of very small platinum particles (e.g., <2 nm and sub-nm in diameter) and/or any unreduced Pt(II) species on the carbon support in the as-synthesized catalyst are thought to be structurally more favorable to the dehalogenation reaction. Providing a catalyst having a smaller proportion of these particles has been found to reduce the loss of selectivity to the haloaminoaromatic product resulting from dehalogenation. Larger platinum particles on the carbon support surface have been found to be more stable under reaction conditions and structurally less favorable to dechlorination mechanism. Accordingly, the processes of the present invention provide for a reduction in the loss of selectivity to dechlorination. For example, for the hydrogenation of 2,5-dichloronitrobenzene to 2,5-dichloroaniline, the loss of selectivity from 2,5-dichloroaniline to 2-chloroaniline and 3-chloroaniline can be less than about 0.4 mol. %, less than about 0.3 mol. %, or less than about 0.2 mol. %.

In accordance with various embodiments of the present invention, the hydrogenation catalyst exhibits a reduced population of smaller platinum metal particles or crystallites (e.g., metal particles having a particle size in their largest dimension of less than about 2 nm). These less desirable smaller metal particles are also more susceptible to leaching than larger particles, particularly when the catalyst is used in an acidic environment that has the potential to solubilize platinum metals. Catalysts exhibiting a platinum particle size distribution in which the proportion of smaller metal particles or crystallites is reduced may be obtained using the strategies described herein.

As noted, the hydrogenation reaction can result in the formation of undesired dehalogenation compounds. However, some of these dehalogenation compounds may be more easily separated from certain reaction products than others. For example, processes for producing 3,6-dichloro-2-methoxybenzoic acid (dicamba) include the step of reducing 2,5-dichloronitrobenzene to 2,5-dichloroaniline, as described herein. The hydrogenation reaction product can comprise dehalogenation compounds such as 2-chloroaniline and 3-chloroaniline. In a subsequent step of the dicamba production process, 2,5-dichloroaniline is converted to 2,5-dichlorophenol. During this conversion, 2- and 3-chloroaniline are converted to 2- and 3-monochlorophenol, respectively. 3-Chlorophenol is difficult to separate from 2,5-dichlorophenol via distillation because of its close boiling point to 2,5-dichlorophenol (214° C. vs. 211° C.). On the other hand, 2-monochlorophenol has a much lower boiling point (175° C.) than 2,5-dichlorophenol, which provides for a more effective separation via distillation. Thus, in this case, assuming dehalogenation cannot be entirely eliminated, then 2-chloroaniline is a preferred dehalogenation compound over 3-chloroaniline.

It has been further discovered that dechlorination selectivity (e.g., selectivity to 2-chloroaniline over 3-chloroaniline) is also dependent on platinum particle size of the platinum catalyst. Without being bound by theory, this structure sensitivity of dechlorination is likely due to the platinum particle size effect where smaller platinum particles have a more open structure providing less steric hindrance to the bulky ortho-Cl atom that is positioned next to the amine group that binds onto the platinum site. As such, this particle structure is thought to lead to the formation of 3-chloroaniline. In the case of larger platinum particles, the steric effect from the neighboring platinum atoms on the ortho-Cl atom is thought to lower the pre-exponential factor of the Arrhenius equation (collision frequency), thus lowering the rate of formation of 3-chloroaniline. Accordingly, various processes of the present invention for hydrogenating 2,5-dichloronitrobenzene to 2,5-dichloroaniline provide for a reduced mole ratio of 3-chloroaniline to 2-chloroaniline in the reaction product. In various embodiments, the mole ratio of 3-chloroaniline to 2-chloroaniline in the reaction product is no greater than about 6:1, no greater than about 5:1, no greater than about 4:1, no greater than about 3:1, no greater than about 2:1, or no greater than about 1:1. For example, the mole ratio of 3-chloroaniline to 2-chloroaniline can range from about 0.5:1 to about 6:1, from about 0.5:1 to about 5:1, from about 0.5:1 to about 4:1, from about 0.5:1 to about 3:1, from about 0.5:1 to about 2:1, from about 1:1 to about 6:1, from about 1:1 to about 5:1, from about 1:1 to about 4:1, from about 1:1 to about 3:1, or from about 1:1 to about 2:1.

Hydrogenation Catalyst

Methods used to deposit the platinum onto the surface of the carbon support are generally known in the art, and include liquid phase methods such as reaction deposition techniques (e.g., deposition via reduction of platinum metal compounds, and deposition via hydrolysis of platinum metal compounds), ion exchange techniques, excess solution impregnation, and incipient wetness impregnation; vapor phase methods such as physical deposition and chemical deposition; precipitation; electrochemical deposition; and electroless deposition. Deposition of platinum onto the carbon support may comprise, for example, reductive deposition wherein a surface of a carbon support is contacted with a solution comprising reducing agent and a compound comprising the platinum. Reducing agents, include for example, formaldehyde, formic acid, hydrazine, citric acid, polyols (e.g., ethylene glycol), and sodium borohydride.

As noted, the hydrogenation catalysts used in the processes of the present invention comprise noble metal (e.g., platinum) particles on the surface of a carbon support. The presence of very small platinum particles and/or any unreduced Pt(II) species on the carbon support in the catalyst are thought to be structurally more favorable to the dehalogenation reaction. Providing a catalyst having a smaller proportion of these particles has been found to reduce the loss of selectivity to the haloaminoaromatic product resulting from dehalogenation. In accordance with the present invention, one strategy for providing a catalyst having a reduced proportion of platinum particles of less than 2 nm and a smaller proportion of unreduced Pt(II) species is to subject the catalyst to a calcination treatment. Subjecting the catalyst to a calcination treatment generally affects the particle size distribution of platinum metal particles present on the surface of the carbon support. In particular, high temperatures of the calcination induces controlled agglomeration of small platinum particles on the carbon surface thereby forming larger platinum particles, which are more stable and structurally less favorable to the dechlorination reaction. Also, calcination reduces the proportion of unreduced Pt(II) species such that the hydrogenation catalyst has a Pt(II) content that is less than about 0.1 wt. %, less than about 0.05 wt. %, or less than about 0.01 wt. % of the total weight of platinum. Accordingly, processes of the present invention include use of a calcined hydrogenation catalyst.

Temperatures below 500° C. are generally unsatisfactory for calcination. On the other hand, subjecting the catalyst to temperatures in excess of 1200° C. promotes graphitization of the carbon support and/or over-sintering of the metal particles. Graphitization of the carbon support and over-sintering of the metal particles tends to reduce the activity of the catalyst by reducing the surface areas of catalytically active carbon and platinum metal. In addition, such a reduction in exposed surface area of catalytically active platinum metal is an uneconomical use of costly platinum metal. Thus, generally, the catalyst is heated to a temperature of at least about 500° C., for example from about 500° C. to about 1200° C.

To attain a catalyst exhibiting the desired particle size distribution, the surface of the catalyst is typically heated to a temperature of at least about 600° C., at least about 700° C., at least about 800° C., or at least about 900° C. For example, the catalyst can be subjected to a heat treatment temperature of from about 500° C. to about 1000° C., from about 600° C. to about 1000° C., from about 700° C. to about 1000° C., from about 800° C. to about 1000° C., from about 500° C. to about 950° C., from about 600° C. to about 950° C., from about 700° C. to about 950° C., or from about 800° C. to about 950° C. In particular, heating the surface of the carbon support to a temperature at least as high as these minimums and within these ranges, has an advantageous effect in promoting the formation of platinum metal particles on the surface of the carbon support having a particle size distribution in which the population of smaller metal particles (e.g., those particles less than about 2 nm or less in their largest dimension) is reduced. Calcination also enhances the stability of the catalyst because larger platinum particles on the carbon support are more resistant to leaching than smaller particles.

Typically, the catalyst is calcined in an inert, non-oxidizing environment. The inert, non-oxidizing environment may consist essentially of inert gases such as nitrogen, noble gases (e.g., argon, helium) or mixtures thereof.

It is optionally for hydrogen to be present in the non-oxidizing environment of the calcination process due to the small molecular size of the hydrogen that allows better penetration into the deepest pores of the carbon support. The concentration of hydrogen may vary, although hydrogen contents of no more than about 5% by volume are preferred. Typically, hydrogen can be present in the calcination atmosphere at a concentration of from about 1 to about 5% by volume and, more typically, from about 2 to about 5% by volume. The remainder of the gas may consist essentially of a non-oxidizing gas such as nitrogen, argon, or helium. Such non-oxidizing gases may be present in the calcination atmosphere at a concentration of at least about 90% by volume, from about 90 to about 99% by volume, and from about 95 to about 98% by volume.

Calcination following metal deposition can comprise high-temperature gas-phase reduction to remove oxygen-containing functional groups from the surface of the catalyst, thereby attaining a catalyst exhibiting the carbon monoxide desorption and/or carbon atom to oxygen atom surface ratio characteristics as described in U.S. Pat. No. 6,417,133.

As the number of smaller platinum particles is reduced, the surface area of exposed metal on the carbon support also decreases. The total exposed metal surface area of catalysts of the present invention may be determined using static carbon monoxide chemisorption analysis.

Exposed metal surface area (m² per gram catalyst) may be determined from the volume of CO chemisorbed using the following equation:

$$\text{Metal surface area (m}^2\text{/g catalyst)} = 6.023 \times 10^{23} \times V / 2 \times SF \times A / 22{,}414 \text{, where:}$$

$V$ = volume of CO chemisorbed (cm³/g STP) (Volume of one mole of gas is 22,414 cm³ STP, i.e., the volume of one µmole of CO is 0.022414 cm³)

SF=stoichiometry factor (assumed to be equal to 1, i.e., one CO molecule per exposed Pt atom)

A=effective area of one exposed Pt atom (m$^2$/atom) (8×10$^{-20}$ m$^2$/atom of Pt)

A further strategy for providing a catalyst having a reduced proportion of platinum particles of less than 2 nm involves calcining an unreduced platinum catalyst precursor. In this strategy, unreduced platinum is deposited on a carbon support to form the catalyst precursor (i.e., deposited without use of a reducing agent). Subsequently, the catalyst precursor is calcined as described herein. Calcination at the temperatures stated herein reduces the platinum metal and results in more platinum agglomeration, which can lower the proportion of small platinum particles on the catalyst.

Other techniques to modify the platinum particle size distribution of the hydrogenation catalyst include procedures for the controlled hydrolysis and deposition of platinum precursors onto activated carbon to achieve larger platinum clusters (e.g., using polyols, stronger reducing agents, pre-formed colloidal Pt or Pt-ligand complexes).

Another strategy for providing a catalyst having a reduced proportion of platinum particles of less than 2 nm involves modifying the carbon support prior to platinum deposition by selectively blocking relatively small pores (e.g., micropores). Pore blocking preferentially prevents deposition of platinum within pores that would be inaccessible to one or more reactants. Pore blockers used to selectively block micropores may be selected from a variety of compounds including, for example, various sugars (e.g., sucrose), 5- or 6-member ring-containing compounds (e.g., 1,3- and 1,4-disubstituted cyclohexanes), and combinations thereof. Compounds suitable for use in connection with selective blocking of micropores include 1,4-cyclohexanedimethanol (1,4-CHDM), 1,4-cyclohexanedione bis(ethylene ketal), 1,3- or 1,4-cyclohexanedicarboxylic acid, 1,4-cyclohexane dione monoethylene acetal, and combinations thereof.

The pore blockers may comprise the product of a reaction (e.g., a condensation reaction) between one or more pore blocking compound precursors. Once formed, the resulting pore blocking compound may be preferentially retained within selected pores of the support by virtue of having at least one dimension that prevents the pore blocking compound from exiting the pores.

For example, it has been observed that the coupling product of a cyclohexane derivative and a glycol may be utilized as a micropore pore blocking agent for particulate carbon supports used to support a platinum metal or other metal catalyst. More particularly, the pore blocking agent may be the coupling product of a di-substituted, tri-substituted, or tetra-substituted cyclohexane derivative and a glycol. In particular, the cyclohexane derivative may be selected from the group consisting of 1,4-cyclohexanedione, 1,3-cyclohexanedione, 1,4-cyclohexanebis(methylamine), and combinations thereof. The glycol is generally selected from the group consisting of ethylene glycol, propylene glycol, and combinations thereof.

Generally, the support is contacted with a liquid comprising the pore blocking agent or one or more precursor(s) of the pore blocking agent. Typically, the support to be treated is contacted with a mixture or solution comprising one or more pore blocking compounds or precursor(s) dispersed or dissolved in a liquid contacting medium (e.g., deionized water). For example, the support may be contacted with a mixture or solution including a cyclohexane derivative and a glycol, or a liquid contacting medium consisting essentially of the cyclohexane derivative and glycol. The support may also be sequentially contacted with liquids or liquid media comprising one or more of the precursors.

Regardless of whether a compound that ultimately functions as a pore blocker is introduced into pores of the support or precursors that form the blocking compound are introduced into the support, pore blockers may be preferentially retained within selected support pores (e.g., micropores) by virtue of the conformational arrangement assumed by the pore blocking agent once disposed or formed within the pores. For example, it is currently believed that various pore blocker molecules transform from a more linear chair conformation to a bulkier boat conformation, which conduces trapping of the compound within the micropores. In particular, it is currently believed that various pore blocking agents including a hydrophilic end group will favor a boat conformation within the micropore(s) of a porous carbon support because of the nature of the carbon support (i.e., the boat conformation will be favored by a pore blocking compound having hydrophilic end groups because of the relatively hydrophobic nature of the carbon support surface). Examples of pore blocking compounds including a hydrophilic end group include 1,4-cyclohexanedicarboxylic acid and 1,4-cyclohexanedimethanol (CHDM).

A conformational change of a pore blocker also may be promoted or induced by manipulating the liquid medium comprising the pore blocking agent in contact with the support including, for example, adjusting the pH and/or adjusting the temperature of the liquid medium.

As noted, it is believed that contacting the support with the pore blocking agent or precursors results in pore blocking agent being introduced into or disposed within support micropores, and within larger pores outside this predefined range. In order to provide a treated support in which the micropores within the predefined range are preferentially blocked, the support is subsequently contacted with a washing liquid to remove the blocking agent from pores outside the micropore domain (i.e., those pores in which the pore blocking agent will not be preferentially retained by virtue of the agent having at least one dimension larger than the pore opening).

Employing one or more of these strategies provides a catalyst having a reduced proportion of platinum particles that are less than 2 nm. In various embodiments, the platinum particles of the catalyst are characterized as having a particle size distribution (as determined using electron microscopy) such that with respect to platinum metal particles of a size up to 10 nm in their largest dimension, no more than about 50% (number basis), no more than about 25% (number basis), no more than about 20% (number basis), no more than about 15% (number basis), or no more than about 10% (number basis) of the platinum metal particles are less than 2 nm in their largest dimension. Also, at least about 25% (number basis, at least about 40% (number basis), at least about 50% (number basis) or at least about 60% (number basis), at least about 70% (number basis), or at least about 80% (number basis) of the platinum metal particles up to 10 nm in their largest dimension are from 2 nm to 10 nm in their largest dimension.

Generally, the platinum metal particles up to 10 nm in their largest dimension can be characterized as having average particle size of greater than about 2.5 nm, greater than about 3 nm, greater than about 4 nm, or greater than about 5 nm. The average particle size of the platinum metal particles up to 10 nm in their largest dimension can range from about 2.5 to about 8 nm, from about 3 to about 7 nm, from about 3 to about 6 nm, or from about 3 to about 4 nm.

The particle size distribution of platinum metal particles at the surface of the carbon support may be determined using various techniques known in the art, including electron microscopy. The particle size distribution is characterized with respect to particles of a size less than 10 nm in their largest dimension. However, it should be recognized that the catalyst of the present invention may contain larger particles (e.g., from 10 to 15 nm or even larger).

The hydrogenation catalyst typically has a platinum loading that is no greater than about 5 wt. % of the total catalyst weight. Although higher platinum loadings may provide for a greater amount of catalytic sites, it has been found that lower platinum loadings are suited for the hydrogenation reaction, which beneficially reduces catalyst costs. Accordingly, the hydrogenation catalyst can have a platinum loading that is no greater than about 4 wt. %, no greater than about 3 wt. %, no greater than about 2 wt. %, no greater than about 1.5 wt. %, or no greater than about 1 wt. % of the total catalyst weight. For example, the hydrogenation catalyst can have a platinum loading that is from about 0.1 wt. % to about 5 wt. %, from about 0.1 wt. % to about 4 wt. %, from about 0.1 wt. % to about 3 wt. %, from about 0.1 wt. % to about 2 wt. %, from about 0.1 wt. % to about 1.5 wt. %, from about 0.1 wt. % to about 1 wt. %, from about 0.5 wt. % to about 5 wt. %, from about 0.5 wt. % to about 4 wt. %, from about 0.5 wt. % to about 3 wt. %, from about 0.5 wt. % to about 2 wt. %, from about 0.5 wt. % to about 1.5 wt. %, or from about 0.5 wt. % to about 1 wt. % of the total catalyst weight.

As noted, the hydrogenation catalyst comprises platinum on a carbon support. Preferably, the carbon support of the hydrogenation catalyst comprises activated carbon. Activated, non-graphitized carbon supports are preferred. These supports are characterized by high adsorptive capacity for gases, vapors, and colloidal solids and relatively high specific surface areas. The support suitably may be a carbon, char, or charcoal produced by means known in the art, for example, by destructive distillation of wood, peat, lignite, coal, nut shells, bones, vegetable, or other natural or synthetic carbonaceous matter, but preferably is "activated" to develop adsorptive power. Activation usually is achieved by heating to high temperatures (e.g., >800° C.) with steam or with carbon dioxide which brings about a porous particle structure and increased specific surface area.

The carbon support of the hydrogenation catalyst generally possesses a relatively large surface area. The total specific surface area of the carbon support, as measured by the Langmuir method using $N_2$, is typically at least about 500 $m^2/g$, at least about 600 $m^2/g$, at least about 800 $m^2/g$, more preferably at least about 900 $m^2/g$, at least about 1000 $m^2/g$, at least about 1100 $m^2/g$, or at least about 1200 $m^2/g$. For example, the total specific surface area of the carbon support, as measured by the Langmuir method using $N_2$ can be from about 500 $m^2/g$ to about 3000 $m^2/g$, from about 750 $m^2/g$ to about 3000 $m^2/g$, from about 1000 $m^2/g$ to about 3000 $m^2/g$, from about 1250 $m^2/g$ to about 3000 $m^2/g$, or from about 1500 $m^2/g$ to about 3000 $m^2/g$. In certain embodiments, the total surface area of the support is from about 1500 $m^2/g$ to about 2000 $m^2/g$ or from about 2500 $m^2/g$ to about 3000 $m^2/g$. It is understood that these values generally correspond to those measured by the likewise well-known Brunauer-Emmett-Teller (B.E.T.) method using $N_2$.

The Langmuir surface area of the carbon support attributable to pores having a diameter of less than 2 nm (i.e., micropores) is typically at least about 750 $m^2/g$, at least 1000 $m^2/g$, or at least about 1250 $m^2/g$. The Langmuir micropore surface area of the carbon support can be from about 750 $m^2/g$ to about 2000 $m^2/g$, from about 1000 $m^2/g$ to about 2000 $m^2/g$, or from about 1250 $m^2/g$ to about 2000 $m^2/g$. The Langmuir surface area of the carbon support attributable to pores having a diameter of greater than 2 nm (i.e., mesopores and macropores) can be from about 100 $m^2/g$ to about 1000 $m^2/g$, from about 200 $m^2/g$ to about 800 $m^2/g$, or from about 300 $m^2/g$ to about 800 $m^2/g$.

As indicated, a relatively large portion of the surface area of the carbon support can be attributable to micropores. In various embodiments, at least about 50%, at least about 60%, at least about 70%, or at least about 80% of the total Langmuir surface area of the carbon support is attributable to micropores. In these and other embodiments, from about 50% to about 90%, from about 60% to about 90%, or from about 65% to about 85% of the total Langmuir surface area of the carbon support is attributable to micropores.

The carbon support can also have an average pore diameter that is in the range of from about 0.5 nm to about 5 nm, from about 1 nm to about 5 nm, from 1 nm to about 4 nm, from about 1 nm to about 3 nm, or from about 2 nm to about 5 nm. Further in accordance with the present invention, the carbon support can have a pore volume of at least about 0.3 ml/g, at least about 0.4 ml/g, or at least about 0.5 ml/g. The carbon support can have a pore volume of from about 0.1 to about 2.5 ml/g, from about 0.2 to about 2.0 ml/g, or from about 0.4 to about 1.5 ml/g. Also, the carbon support can have a pore volume that is from about 0.3 ml/g to about 0.1 ml/g, or from about 0.5 ml/g to about 0.1 ml/g that is attributable to pores of a diameter from 0.5 nm to 5 nm.

The support can be a monolithic support. Suitable monolithic supports may have a wide variety of shapes. Such a support may be, for example, in the form of a screen or honeycomb. In various embodiments, the supports are in the form of particulates. Suitable particulate supports may have a wide variety of shapes. For example, such supports may be in the form of granules. The support can also be in the form of a powder or particulate. These particulate supports may be used in a reactor system as free particles, or may be bound to a structure in the reactor system, such as a screen or an impeller.

One approach commonly used to suppress the dehalogenation of the haloaminoaromatic product is through the incorporation of a catalyst modifier in the form of a metal promoter (e.g., copper, nickel, ruthenium; either as alloy or co-metal, on the platinum on carbon catalyst) or a non-metal added to the catalyst (e.g., a sulfide-treated platinum on carbon catalyst). However, incorporation of a catalyst modifier may lead to additional impurities (e.g., leached catalyst metal) requiring removal. The catalyst modifier may also catalyze other undesirable side-reactions, which could also introduce further impurities that may require separation from the reaction mixture from the hydrogenation step or subsequent process steps. Avoiding the use of additional catalyst modifiers can also reduce catalyst cost.

Advantageously, the hydrogenation catalyst used in hydrogenation processes of the present invention can be essentially free or free of modifiers. In other words, the hydrogenation catalyst used in hydrogenation processes of the present invention can be an unmodified hydrogenation catalyst. As used herein, the term "modifier" refers to an additional component that is added to the catalyst. Thus, the term "unmodified hydrogenation catalyst" does not refer to a catalyst that has been altered by processes, such as calcination, that do not introduce one or more additional components to the catalyst.

Catalyst modifiers include various metal promoters. Accordingly, in various embodiments, the hydrogenation catalyst can be a non-promoted catalyst. That is, metal promoters (or dopants) are not required and can be avoided for various processes of the present invention. In various embodiments, the metal promoters are transition metals. For example, the metal promoters can be selected from the group consisting of copper, nickel, iron, and combinations thereof. In these and other embodiments, the metal promoters can be alkali and alkali earth metals. As used herein, the term "metal" includes various forms of the metal including elemental, metal oxide, metal hydroxides, metal ions, etc.

However, certain trace metals (i.e., metals besides platinum) may be present as impurities in the carbon support, impurities in the platinum deposited on the support, and/or impurities in the feed mixture (e.g., metal leached from reaction vessels/piping or upstream catalysts). In various embodiments, the trace metal content of the hydrogenation catalyst is no greater than about 0.1 wt. %, no greater than about 0.05 wt. %, no greater than about 0.01 wt. %, no greater than about 0.005 wt. %, or no greater than about 0.001 wt. % of the total weight of the catalyst. The trace metal content of the hydrogenation catalyst can be from about 0.0001 wt. % to about 0.1 wt. %, from about 0.0001 wt. % to about 0.05 wt. %, from about 0.0001 wt. % to about 0.01 wt. %, from about 0.0001 wt. % to about 0.005 wt. %, or from about 0.0001 wt. % to about 0.001 wt. % of the total weight of the catalyst.

The hydrogenation catalyst used in processes of the present invention can also be essentially free or free of other non-metal catalyst modifiers (e.g., catalyst poisons). For example, the hydrogenation catalyst can be free or essentially free of non-metal catalyst modifiers such as sulfide.

In various embodiments, the hydrogenation catalyst that is introduced into the hydrogenation zone consists or consists essentially of platinum on a carbon support. A catalyst that "consists essentially of" a carbon support and platinum would therefore include all components and minor substituents of the carbon support (typically an activated carbon support) plus the deposited platinum active phase. But, this catalyst does not include any further catalyst modifier deposited on the carbon support surface intended to form a catalytically active phase or modify the catalytically active phase.

Hydrogenation Reaction

The reaction mixture generally comprises hydrogen and the halonitroaromatic reactant (e.g., 2,5-dichloronitrobenzene). Similar to the hydrogenation catalyst, the feed mixture comprising the halonitroaromatic reactant (and reaction mixture) can be essentially free or free of additives that function as dehalogenation suppressors. Dehalogenation suppressors include for example, hydroxides or oxides of magnesium, cycloaliphatic amines such piperazine and morpholine, acidic phosphorous compounds, among others. Thus, various processes of the present invention comprise feeding hydrogen and a feed mixture comprising a halonitroaromatic compound such as 2,5-dichloronitrobenzene to a hydrogenation zone; and reacting the halonitroaromatic compound (e.g., 2,5-dichloronitrobenzene) with hydrogen in the presence of a heterogeneous hydrogenation catalyst to produce a reaction product comprising a haloaminoaromatic compound (e.g., 2,5-dichloroaniline), wherein the hydrogenation catalyst is an unmodified hydrogenation catalyst and the feed mixture is free of dehalogenation suppressors.

The hydrogenation reaction can be conducted with or without a solvent. In various embodiments, the feed mixture comprises a solvent (e.g., water, alcohol, and/or acid). Thus, these processes comprise feeding hydrogen and a feed mixture comprising a halonitroaromatic compound such as 2,5-dichloronitrobenzene and a solvent to a hydrogenation zone; and reacting the halonitroaromatic compound (e.g., 2,5-dichloronitrobenzene) with hydrogen in the presence of a heterogeneous hydrogenation catalyst to produce a reaction product comprising a haloaminoaromatic compound (e.g., 2,5-dichloroaniline), wherein the hydrogenation catalyst comprises platinum on a carbon support.

In various embodiments, the solvent comprises an alcohol. One advantage of using alcohol solvents is that they are generally easier to remove than other solvents, which facilitates the isolation of reaction product. For example the alcohols can be methanol, ethanol, propanol, isopropanol, 1-butanol, 2-butanol, t-butanol, and mixtures thereof.

In various embodiments, the solvent comprises an acid. Without being bound by theory, it is believed that during use of the catalyst, an acidic solvent may be beneficial in reducing the loss of selectivity to dechlorination by reducing the number of small platinum particles (<2 nm) on the catalyst support. Smaller platinum particles are typically less stable than larger platinum particles and can be more readily leached off the carbon support in the acidic environment. Moreover, use of an acidic solvent may be beneficial if the hydrogenation process is integrated with other process steps that also use the same solvent.

The acidic solvent can comprise an organic acid. For example, the organic acid can be selected from the group consisting of formic acid, acetic acid, propionic acid, butyric acid, citric acid, and mixtures thereof. In certain embodiments, the organic acid comprises acetic acid. When using an acidic solvent, the acidic solvent can be from about 20 wt. % to about 95 wt. %, from about 30 wt. % to about 95 wt. %, from about 40 wt. % to about 95 wt. %, from about 50 wt. % to about 95 wt. %, from about 60 wt. % to about 95 wt. %, or from about 70 wt. % to about 95 wt. % of the feed mixture.

When using an acidic solvent such as acetic acid in the hydrogenation of 2,5-dichloronitrobenzene to 2,5-dichloroaniline, a post-hydrogenation reaction between the product 2,5-dichloroaniline and acetic acid may result in an irreversible loss to 2,5-dichloroacetaniline. This reaction proceeds as follows:

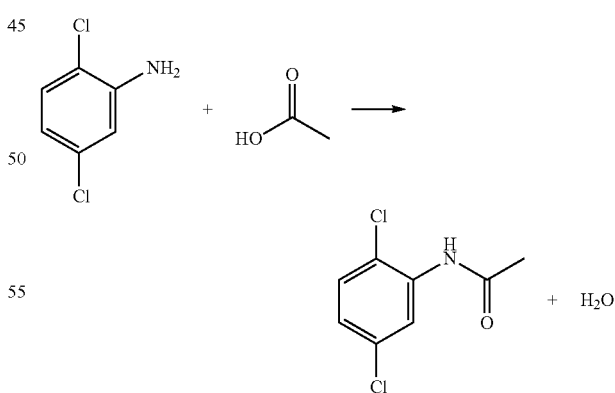

It has been found that this loss to 2,5-dichloroacetaniline can be controlled by subsequently cooling the reaction product to about 15° C. or less or about 10° C. or less. In various processes of the present invention, the reaction product is cooled to a temperature that is between about 0° C. and about 15° C., between about 5° C. and about 15° C., or between about 5° C. and about 10° C. (e.g., about 10° C.).

During the hydrogenation reaction, a portion of the platinum metal of the hydrogenation catalyst may be leached off the carbon support, especially when using an acidic solvent. Consequently, the reaction product can further comprise platinum. Recovery of platinum from the reaction product would further enhance process economics. Accordingly, in various embodiments, the process further comprises recovering platinum from the reaction product.

In the hydrogenation of 2,5-dichloronitrobenzene to 2,5-dichloroaniline, selectivity loss to 2,5-dichloroacetaniline and 2- and 3-chloroaniline has been found to increase with high temperatures, indicating that the acetylation and dechlorination reactions become more favorable as temperature increases. Accordingly, relatively low reaction temperatures are preferred. The hydrogenation reaction can be conducted at a temperature that is from about 20° C. to about 100° C., from about 25° C. to about 100° C., from about 40° C. to about 100° C., from about 40° C. to about 85° C., or from about 40° C. to about 70° C.

Typically, the hydrogenation reaction is conducted under a partial pressure of hydrogen that is at least about 20 kPa, at least about 100 kPa, at least about 200 kPa, or at least about 500 kPa. In various embodiments, the partial pressure of hydrogen is from about 20 kPa to about 2000 kPa, from about 200 kPa to about 1500 kPa, or from about 500 kPa to about 1000 kPa.

The hydrogenation reaction may be carried out in a wide variety of batch, semi-batch, and continuous reactor systems. The configuration of the reactor is not critical. Suitable conventional reactor configurations include, for example, stirred tank reactors, fixed bed reactors, trickle bed reactors, fluidized bed reactors, bubble flow reactors, plug flow reactors, buss loop reactors, and parallel flow reactors.

Process for Producing of 3,6-dichloro-2-methoxybenzoic Acid (Dicamba)

2,5-Dichloroaniline produced in accordance with any of the processes described herein is a useful intermediate in the production of 3,6-dichloro-2-methoxybenzoic acid (dicamba) and salts or esters thereof. International Patent Application Publication WO2015/095284, which is incorporated herein by reference, describes one process for the production of 3,6-dichloro-2-methoxybenzoic acid. In general, this process involves diazotizing 2,5-dichloroaniline to provide 2,5-dichlorobenzenediazonium. The 2,5-dichlorobenzenediazonium is then hydrolyzed to form 2,5-dichlorophenol. Subsequently, 2,5-dichlorophenol is carboxylated to produce 2-hydroxy-3,6-dichlorobenzoic acid (3,6-dichlorosalicylic acid). This intermediate can then be methylated to form a methylation reaction product comprising 3,6-dichloro-2-methoxybenzoic acid salt and/or ester thereof. The methylation product can then be saponified to 3,6-dichloro-2-methoxybenzoic acid. Thus, the hydrogenation processes of the present invention can be further combined with various processes for producing 3,6-dichloro-2-methoxybenzoic acid.

Having described the invention in detail, it will be apparent that modifications and variations are possible without departing from the scope of the invention defined in the appended claims.

EXAMPLES

The following non-limiting examples are provided to further illustrate the present invention.

Example 1: Calcination of Platinum-On-Carbon Catalyst

A 1 wt. % platinum on activated carbon (Pt/C) catalyst was calcined at temperature of 900° C. in a heating tube under an argon atmosphere for approximately two hours. Subsequently, the catalyst was removed from the heating tube and mixed to minimize any non-uniform temperature distribution along the tube. Then, the catalyst was reloaded back into heating tube for a second heat treatment at 900° C. for approximately two hours. Alternatively, the catalyst can be calcined in a rotator tube to achieve the uniform temperature.

Figure 2:
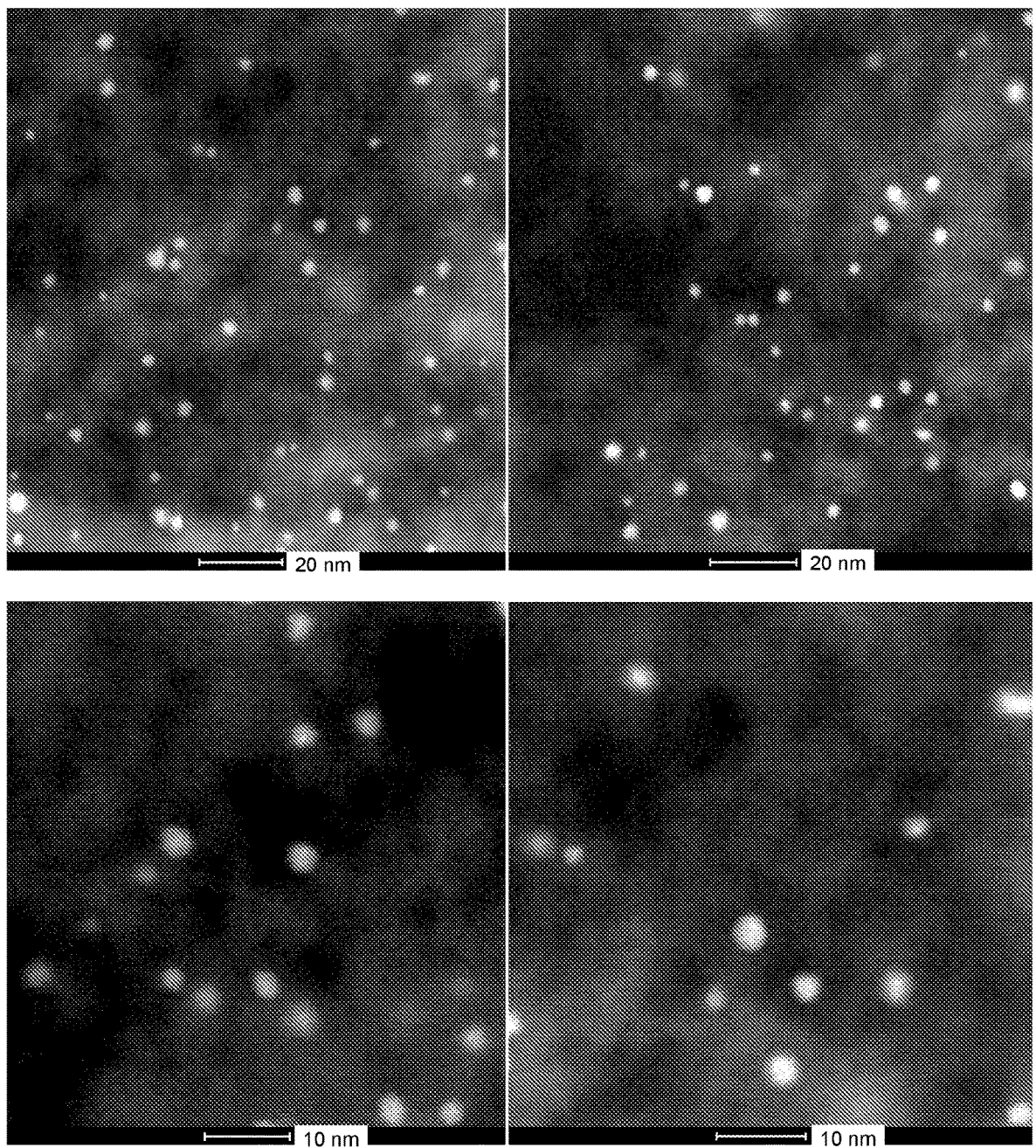
FIG. 2 presents a series of STEM images of the surface of a commercial platinum on carbon catalyst after calcination.
Figure 3:
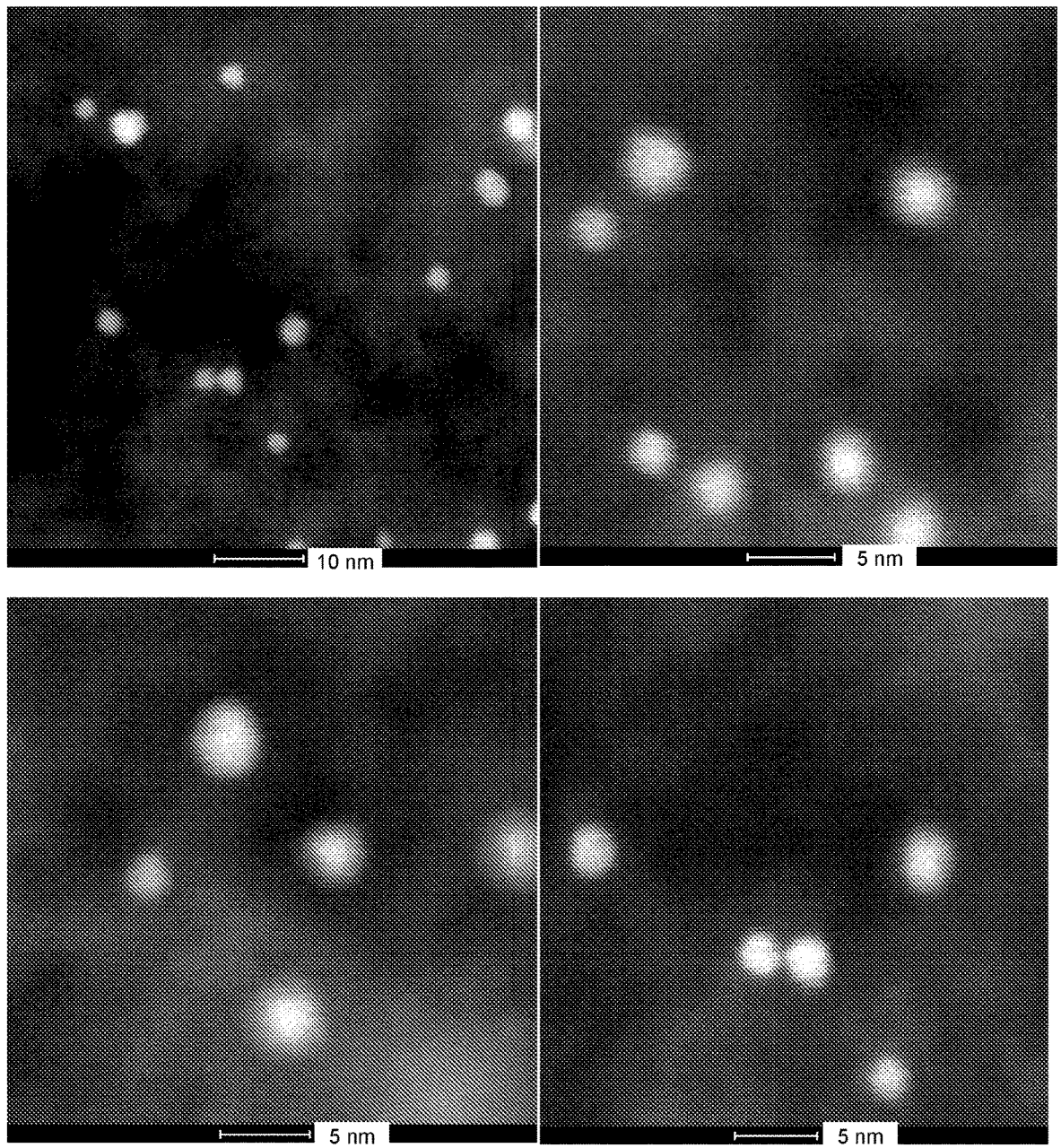
FIG. 3 presents a series of STEM images of the surface of a commercial platinum on carbon catalyst after calcination.

The catalyst surface was imaged before and after the calcination using scanning transmission electron microscopy (STEM). FIG. 1 presents a series of images for the catalyst surface of a commercial Pt/C catalyst prior to calcination. FIGS. 2 and 3 present a series of images for the catalyst surface of a commercial Pt/C catalyst after calcination. These images show that the calcination enhanced the sintering and agglomeration of small platinum particles (<2 nm), which appears to have increased the proportion of larger platinum particles (>2 nm).

Example 2: Hydrogenation of 2,5-Dichloronitrobenzene to 2,5-Dichloroaniline Over Noble Metal Catalyst (General Procedure)

A general procedure for the hydrogenation of 2,5-dichloronitrobenzene to 2,5-dichloroaniline was followed for each cycle. A noble metal (e.g., platinum or palladium) supported catalyst was loaded into a HASTELLOY autoclave reactor (approx. 300 ml) and then the reactor was sealed. A solution of 2,5-dichlorobezene (10 to 30 wt. %) in acetic acid was introduced to the reactor through the inlet and the system was checked for any leaks. The system was purged with nitrogen (i.e., pressurizing the reactor to 239 kPa (20 psig) with nitrogen followed by purging) for three times. After purging, the reactor was pressurized with 239 kPa (20 psig) of nitrogen, and both stirring (1400 rpm) and heating were started. Once the temperature of the mixture reached the desired temperature (e.g., approximately 65° C.), stirring was stopped and the nitrogen was purged. The reactor was then charged with hydrogen gas (e.g., to a pressure of 687 kPa (85 psig)) and stirring (1400 rpm) was restarted. At the end of the reaction, the heating was stopped and the hydrogen in the system was purged. The system was then purged with nitrogen for three times using the same protocol as described above. The reaction mixture was drained through the outlet into a container through a filter. The next cycle was repeated by reloading the 2,5-dichlorobezene solution in acetic acid into the system containing the Pt/C catalyst for hydrogenation.

The reaction mixture collected was analyzed for 2,5-dichloroaniline (2,5-DCA); 2,5-dichloroacetaniline (2,5-DCAN); 2-chloroaniline (2-CA); and 3-chlroaniline (3-CA) by a RP-HPLC method.

Parameters of the hydrogenation reaction were varied as described in the following Examples. For example, the catalyst metal, the catalyst support, the catalyst loading ranged from 100 mg to 800 mg, reaction temperature ranged from 45° C. to 65° C., hydrogen pressure ranged from 377 kPa (40 psig) to 1273 kPa (170 psig), and the concentration of the 2,5-dichlorobezene solution in acetic acid ranged from 10 wt. % to 30 wt. %.

Example 3: Effect of Catalyst Metals and Supports

The hydrogenation procedure of Example 2 was conducted with a variety of catalysts containing different metals (platinum and palladium) and catalyst supports (carbon and silica). The catalysts were 1 wt. % Pt/C, 1 wt. % Pt/SiO$_2$, 1 wt. % Pd/C, and a 5 wt. % Pt/C promoted with 0.5 wt. % Fe (5 wt. % Pt/0.5 wt. % Fe/C). These catalysts were not calcined, with the exception of the 5 wt. % Pt/0.5 wt. % Fe/C catalyst. The 5 wt. % Pt/0.5 wt. % Fe/C catalyst was calcined at a high temperature (approximately 900° C.) prior to use. In each run of the hydrogenation reaction procedure, approximately 755 mg (dry basis) of each catalyst and 150 g of a 30 wt. % 2,5-dichloronitrobenzene in acetic acid were loaded into the reactor. Hydrogen was charged to the reactor at a pressure of 687 kPa (85 psig). The reactor was heated to a temperature of 45° C. The results of these runs after one reaction cycle are provided in Table 1.

TABLE 1

Metal and Support of Catalyst vs. Dechlorination

| | Catalyst Lot # | | | | |
|---|---|---|---|---|---|
| | | | Lot 1 | Lot 2 | |
| Metal | Pt | Pd | Pt | Pt | Pt—Fe |
| Metal Loading (wt. %) | 1% | 1% | 1% | 1% | 5%/0.5% |
| Catalyst Support | $SiO_2$ | Carbon | Carbon | Carbon | Carbon |
| 2,5-DCAN (mol. %) | 0.19 | 0.19 | 0.12 | 0.11 | 0.09 |
| 2-CA + 3-CA (mol. %) | 0.44 | 2.98 | 0.71 | 0.60 | 0.15 |
| 3-CA/2-CA Ratio | 6.00 | 1.20 | 4.10 | 3.70 | 0.85 |
| Reaction time (min) | 202 | 291 | 64 | 68 | 62 |
| Conversion (%) | 90.0 | 98.9 | 99.8 | 99.8 | 99.7 |

Among the catalysts used, both the Pd/C and Pt/$SiO_2$ catalysts were observed to be less favored for the hydrogenation reaction. The Pd/C catalyst was relatively less active for converting 2,5-dichloronitrobenzene to 2,5-dichloroaniline by hydrogenation, as demonstrated that the reaction was completed in much longer time (i.e., about 300 minutes) and the loss to chloroaniline (i.e., approximately 3 mol. %) was significantly higher compared to platinum catalysts. The Pt/$SiO_2$ catalyst was also less active, as demonstrated by the conversion of about 90% after 200 minutes. In addition, this type of Pt/$SiO_2$ catalyst disintegrated in the reaction mixture. As a result, a considerable amount of catalyst material passed through the reactor frits and collected in the reaction product. The catalyst loss on each cycle was much higher for the Pt/$SiO_2$ catalyst as compared to the other catalysts on carbon support (i.e., about 12% vs. about 5%). Because of longer reaction time with the Pd/C and Pt/$SiO_2$ catalysts, the selectivity loss to 2,5-dichloroacetaniline (2,5-DCAN) was observed to be higher as compared to the Pt/C catalysts.

The 1 wt. % Pt/C catalysts were much more active compared to the 1 wt. % Pd/C and 1 wt. % Pt/$SiO_2$ and had a similar activity to the 5 wt. % Pt/0.5 wt. % Fe/C catalyst, as indicated by the reaction time to achieve at least about 99% conversion. However, the selectivity loss to 2-chloroaniline and 3-chloroaniline was significantly higher with the Pt/C catalyst as compared to the 5 wt. % Pt/0.5 wt. % Fe/C catalyst. Furthermore, dechlorination, particularly at the ortho-position of the 2,5-dichloroaniline product (resulting in 3-CA) was increased with the platinum-only catalysts (including Pt/$SiO_2$), as indicated by the increased ratio of 3-CA/2-CA. The greater selectivity loss towards 2- or 3-chloroanilines using these catalysts could be due to the presence of smaller sized platinum particles (<2 nm) on the carbon support which are thought to favor the formation of monochloroaniline.

The 5 wt. % Pt/0.5 wt. % Fe/C catalyst was evaluated for the hydrogenation reaction. This catalyst was calcined at a high temperature (approximately 900° C.) prior to use. This catalyst is understood to have larger platinum particles (e.g., average size of approx. 7 nm) than the other platinum catalysts listed in Table 1. This type of catalyst was observed to provide a reduced amount of selectivity loss to 2- and 3-chloroaniline due to dechlorination and the highest selectivity to 2-chloroaniline as indicated by a decreased ratio of 3-CA/2-CA.

Example 4: Effect of Hydrogen Pressure, Reaction Temperature, and Reaction Solvent Example 2 was repeated with a commercial 1 wt. % Pt/C catalyst, which was used without being calcined. In these runs of the hydrogenation reaction procedure, approximately 755 mg (dry basis) of the catalyst and 150 g of a 30 wt. % 2,5-dichloronitrobenzene in acetic acid were loaded into the reactor. The amount of hydrogen charged to the reactor was varied between runs at pressures of 474 kPa (54 psig), 687 kPa (85 psig), and 860 kPa (110 psig). The temperature of the reactor was also varied at either 45° C. or 65° C. The results of these runs after one reaction cycle are provided in Table 2-A.

TABLE 2-A $H_2$ Pressure and Reaction Temperature vs. Loss to 3-Chloroaniline

| Cycle # | $H_2$ Pressure | Reaction Temperature (° C.) | 3-CA (mol. %) | Reaction time (Minute) |
|---|---|---|---|---|
| 1 | 474 kPa (54 psig) | 65 | 0.29 | 93 |
| 2 | 474 kPa (54 psig) | 45 | 0.21 | 95 |
| 3 | 860 kPa (110 psig) | 65 | 0.59 | 31 |
| 4 | 860 kPa (110 psig) | 45 | 0.36 | 42 |
| 5 | 687 kPa (85 psig) | 45 | 0.32 | 57 |
| 6 | 687 kPa (85 psig) | 65 | 0.56 | 41 |

Higher hydrogen pressure and higher reaction temperature accelerated the hydrogenation reaction, but dechlorination to 3-chloroaniline was also favored. Therefore, the hydrogen pressure of 87 kPa (85 psig) and the reaction temperature of 45° C. were selected for the further evaluation.

In another set of experiments, Example 2 was repeated with a commercial 1 wt. % Pt/C catalyst, which was used without being calcined; and the reaction solvent was varied between runs. In these runs of the hydrogenation reaction procedure, approximately 755 mg (dry basis) of the catalyst and 150 g of a 30 wt. % 2,5-dichloronitrobenzene in a solvent (i.e., either acetic acid or methanol) were loaded into the reactor. The amount of hydrogen charged to the reactor was 687 kPa (85 psig), and the temperature of the reactor was at 45° C. The results of these runs after three reaction cycles are provided in Table 2-B.

TABLE 2-B

Reaction Solvent vs. Dechlorination and Reaction time

| Solvent | Cycle # | 2-CA + 3-CA (mol. %) | 3-CA (mol. %) | 3-CA/2-CA Ratio | Reaction time (Minute) |
|---|---|---|---|---|---|
| Acetic Acid | 1 | 0.71 | 0.57 | 4.10 | 64 |
| | 2 | 0.58 | 0.45 | 3.49 | 59 |
| | 3 | 0.64 | 0.50 | 3.77 | 59 |
| Methanol | 1 | 1.13 | 0.94 | 4.91 | 35 |
| | 2 | 0.91 | 0.77 | 5.49 | 32 |
| | 3 | 1.07 | 0.90 | 5.22 | 30 |

The hydrogenation in non-acetic solvent, for example, in methanol, was observed to provide increased dechlorination and reduced reaction time. The higher solubility of hydrogen in methanol than in acetic acid may result in shorter reaction time and more dechlorination. Since the 2,5-dichloroacetaniline (2,5-DCAN) is only formed in acetic acid, it can be eliminated by using methanol as the reaction solvent.

Example 5: Effect of Calcination on Platinum Catalyst

Example 2 was repeated using calcined and un-calcined 1 wt. % Pt/C catalysts. The 1 wt. % Pt/C catalyst was a commercial Pt/C catalyst. Calcination was performed in accordance with the procedure described in Example 1, except that the calcination temperature was varied (e.g., 500° C., 700° C., and 900° C.). In these runs of the hydrogenation reaction procedure, approximately 755 mg (dry basis) of the catalyst and 150 g of a 30 wt. % 2,5-dichloronitrobenzene in acetic acid were loaded into the reactor. Hydrogen was charged to the reactor at a pressure of 687 kPa (85 psig). The reactor was heated to a temperature of 45° C. The results of these runs after one reaction cycle are provided in Table 3.

TABLE 3

Catalyst Calcination Temperature vs. Impurity Profile and Catalyst Activity

| | Catalyst | | | | |
|---|---|---|---|---|---|
| | Lot 1 | Lot 2 | Lot 1 | Lot 1 | Lot 2 |
| Calcination Temperature (° C.) | none | none | 500 | 700 | 900 |
| 2,5-DCAN (mol. %) | 0.12 | 0.11 | 0.07 | 0.12 | 0.13 |
| 2-CA + 3-CA (mol. %) | 0.71 | 0.60 | 0.44 | 0.25 | 0.19 |
| 2-CA (wt. %) | 0.028 | 0.023 | 0.026 | 0.019 | 0.018 |
| 3-CA/2-CA Ratio | 4.1 | 3.7 | 2.6 | 1.7 | 1.1 |
| Reaction time (min) | 64 | 68 | 64 | 74 | 102 |
| Conversion (%) | 99.8 | 99.8 | 99.8 | 99.7 | 99.5 |

The selectivity loss to 2,5-dichloroacetaniline (2,5-DCAN) was observed to be constant regardless of the temperature of calcination of the catalyst. The selectivity loss to 2- and 3-chloroaniline upon dechlorination of 2,5-dichloroaniline decreased considerably as the calcination temperature increased. Furthermore, the 2-chloroaniline level was maintained relatively constant while the 3-chloroaniline was observed to be significantly less, which resulted in a decrease in the ratio of 3-chloroaniline to 2-chloroaniline (3-CA/2-CA). This observation is consistent with the theory that the increase of the size of platinum particles decreases the dechlorination, particularly at the ortho-position of the 2,5-dichloroaniline product. However, the activity of the catalyst decreased slightly as the temperature of the calcination temperature increased as indicated by the longer reaction time.

Example 6: Comparison of Various Platinum Catalysts

Example 2 was repeated using a variety of Pt/C catalysts. The catalysts were a 1 wt. % Pt/C catalyst (used without being calcined), a 1 wt. % Pt/C catalyst that was calcined at 500° C., a 1 wt. % Pt/C catalyst that was calcined at 700° C., a 1 wt. % Pt/C catalyst that was calcined at 900° C., and a 5 wt. % Pt/C catalyst promoted with 0.5 wt. % Fe that was calcined at 900° C. The 1 wt. % Pt/C catalyst was a commercial Pt/C catalyst.

In each run of the hydrogenation reaction procedure, approximately 755 mg (dry basis) of each catalyst and 150 g of a 30 wt. % 2,5-dichloronitrobenzene in acetic acid were loaded into the reactor. Hydrogen was charged to the reactor at a pressure of 687 kPa (85 psig). The reactor was heated to a temperature of 45° C. The results of these runs after a series of reaction cycles are provided in Table 4.

TABLE 4

Catalyst Varieties, Reaction Cycles vs. Dechlorination

| | Catalyst | | | | | | | |
|---|---|---|---|---|---|---|---|---|
| | Pt/C | Pt/C | Pt/C | Pt/C | Pt/Fe/C | Pt/C | Pt/C | Pt/C |
| | | | Calcination Temperature (° C.) | | | | | |
| # of Cycle | none | 500 | 700 | 900 | 900 | none | 700 | 900 |
| | | 2-CA + 3-CA (mol. %) | | | | | 3-CA/2-CA Ratio | |
| 1 | 0.60 | 0.44 | 0.25 | 0.19 | 0.15 | 3.72 | 1.66 | 1.08 |
| 2 | 0.55 | 0.35 | 0.22 | 0.16 | 0.16 | 3.71 | 1.57 | 1.02 |
| 3 | — | 0.34 | 0.22 | — | — | — | 1.47 | — |
| 4 | — | — | — | — | — | — | — | — |
| 5 | 0.59 | — | 0.21 | 0.16 | 0.16 | 3.56 | 1.36 | 0.93 |
| 6 | — | — | — | — | — | — | — | — |
| 7 | — | — | — | — | — | — | — | — |
| 8 | 0.57 | — | 0.19 | 0.16 | 0.16 | 3.23 | 1.07 | 0.91 |
| 9 | — | — | — | — | — | — | — | — |
| 10 | — | — | — | — | — | — | — | — |
| 11 | — | — | — | 0.14 | 0.15 | — | — | 0.94 |
| 12 | 0.53 | — | 0.16 | — | — | 2.68 | 0.90 | — |
| 13 | — | — | — | — | — | — | — | — |
| 14 | — | — | — | — | — | — | — | — |
| 15 | — | — | 0.14 | 0.12 | — | 2.39 | 0.81 | 0.88 |
| 16 | — | — | — | — | — | — | — | — |
| 17 | 0.52 | — | — | — | — | 2.25 | — | — |
| 18 | — | — | — | — | — | — | — | — |
| 19 | — | — | — | — | — | — | — | — |
| 20 | 0.45 | — | — | — | — | 1.99 | — | — |

Selectivity to the preferred dechlorination compound 2-chloroaniline over a number of reaction cycles increased with increasing calcination temperature as indicated by a decreased ratio of 3-CA/2-CA. The 1 wt. % Pt/C catalyst that was calcined at 900° C. provided similar selectivity to the preferred dechlorination compound 2-chloroaniline as compared to the 5 wt. % Pt/0.5 wt. % Fe/C catalyst.

Figure 4:
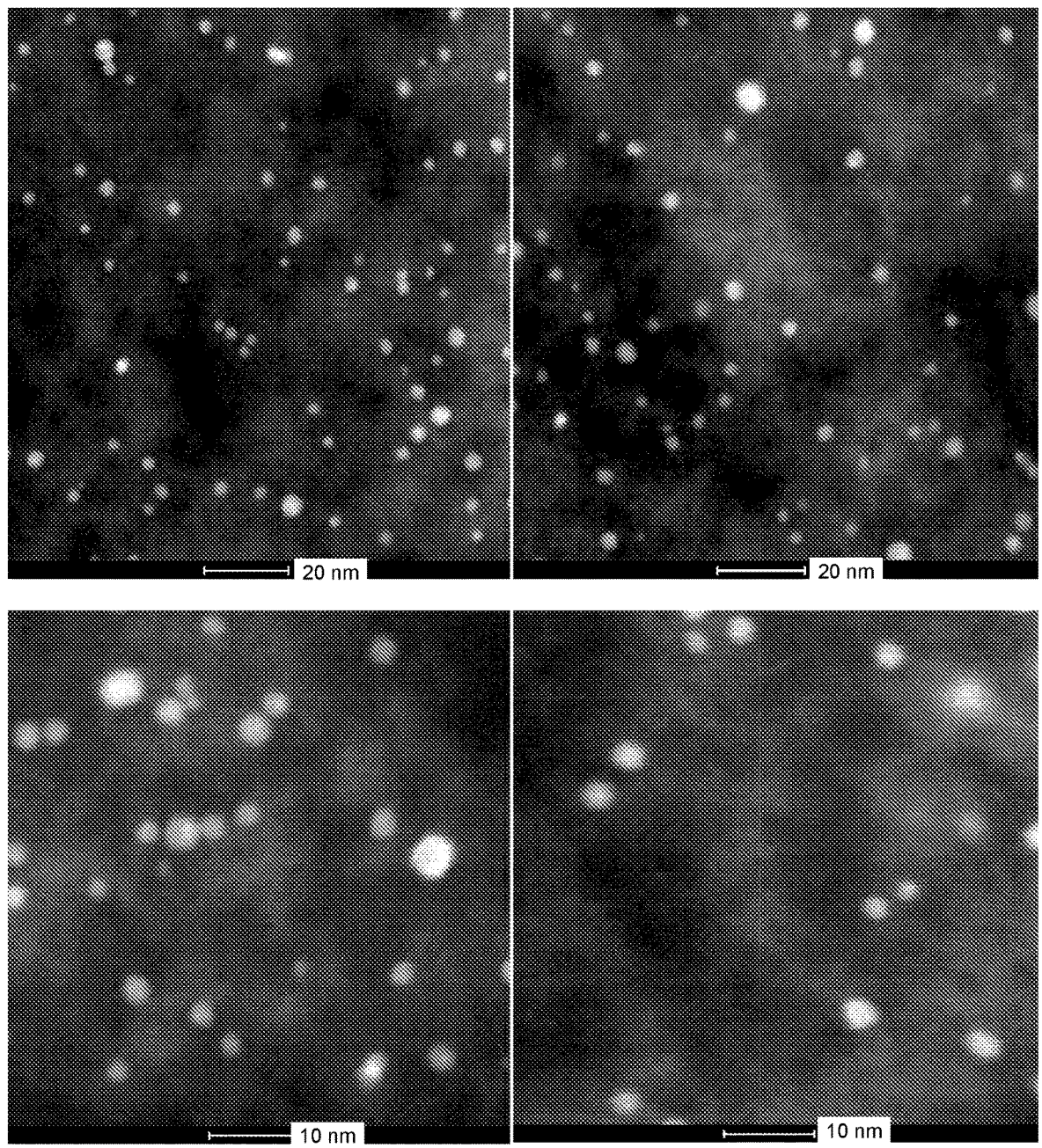
FIG. 4 presents a series of STEM images of the surface of a commercial platinum on carbon catalyst after calcination and after 15 reaction cycles.
Figure 5:
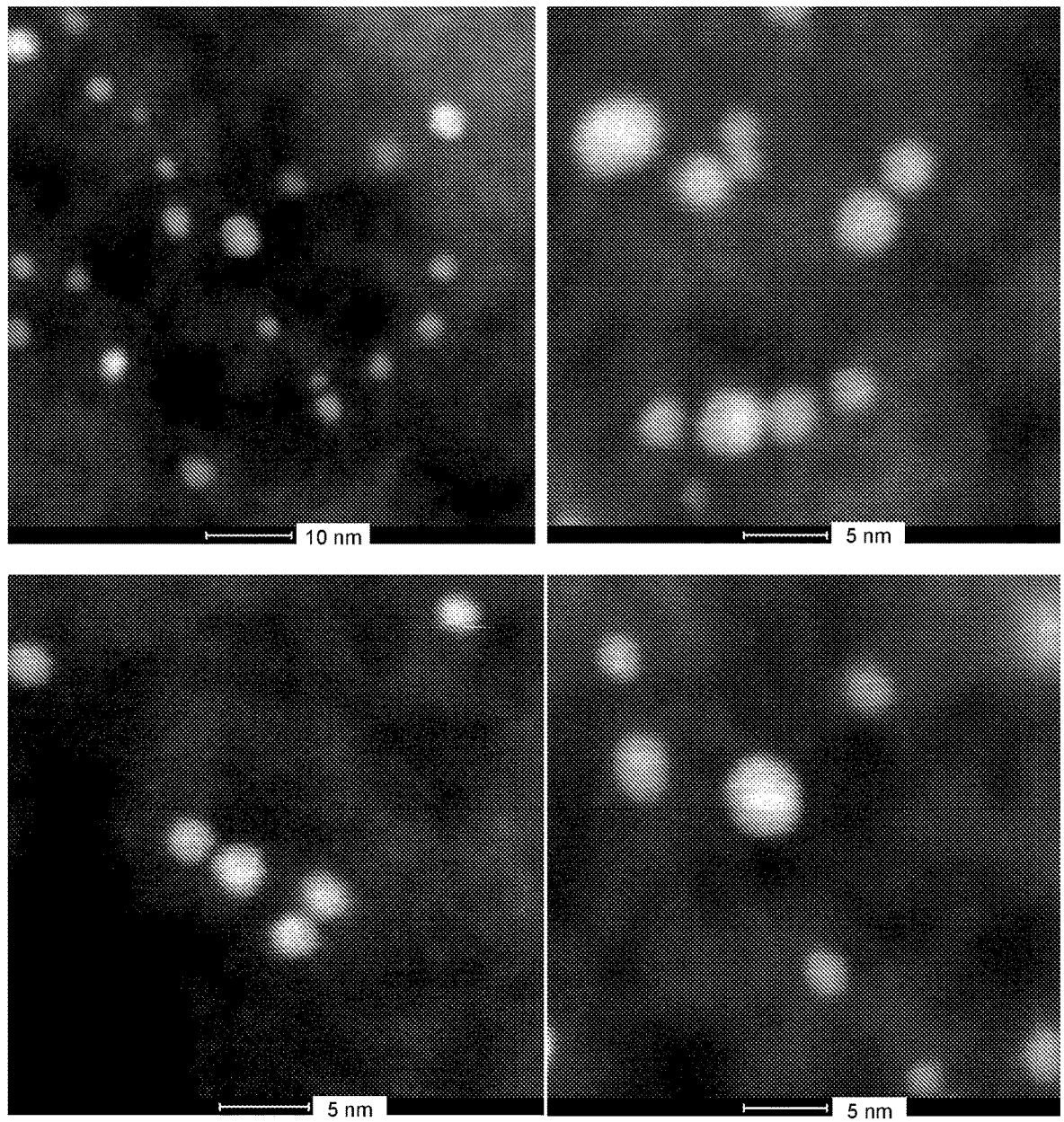
FIG. 5 presents a series of STEM images of the surface of a commercial platinum on carbon catalyst after calcination and after 15 reaction cycles.

To evaluate the stability of a calcined catalyst in the reaction medium, the 1 wt. % Pt/C catalyst that was calcined at 900° C. was imaged using STEM before the first reaction cycle (i.e., fresh catalyst) and then again after 15 cycles. FIGS. 2 and 3 present a series of images for the catalyst surface after calcination, but prior to use. FIGS. 4 and 5 present a series of images for the catalyst surface after 15 reaction cycles. These images show that the catalyst is stable (e.g., resistant to leaching) over the course of numerous reaction cycles.

Example 7: Preparation of 1 wt. % Platinum Catalyst on Activated Carbon (General Procedure)

The following are general procedures for the preparation of a 1 wt. % Pt/C catalyst. The carbon slurry concentration, pH adjustment, the amount of reducing agent (NaBH$_4$), the temperature, and the final pH of the slurry can vary during the process of the preparation. The following methods (Ia, Ib, II, III, IV, V, VI, VII, VIIIa, VIIIb, IX, Xa and Xb) are representative procedures with several variable parameters.

A. Method Ia

Activated carbon (15.0 g) was suspended to form a slurry in de-ionized water (approx. 150 mL) with stirring for about 20 minutes. The pH of the resulting slurry was pH 8.48. A solution of $H_2PtCl_6 \cdot 6H_2O$ (0.40 g) in de-ionized water (approx. 15 mL) was added dropwise to the carbon slurry over a period of about 15 minutes. The pH of the resulting slurry dropped to pH 5.17 upon the completion of addition of the platinum solution. The resulting slurry was stirred for another 30 minutes at ambient temperature. The pH was adjusted to about pH 4.50 with 1 M HCl solution. The slurry was then heated to 60° C. over approximately 30 minutes while the pH was maintained at about pH 4.50 by addition of 1 M NaOH solution. Upon reaching the temperature of 60° C., the pH of the slurry was increased by an increment of 0.5 every 5 minutes with addition of 1 M NaOH solution until about pH 6.00. The stirring of the slurry was continued for 10 minutes at 60° C. and pH 6.0, and then cooled to below approximately 50° C. A solution of $NaBH_4$ in 14 M NaOH (12 wt. %, 0.50 g) was diluted to 5 mL with de-ionized water; and the diluted solution was added dropwise to the aforementioned prepared slurry over 5 minutes. The stirring was continued for another 10 minutes after the addition, and then heated to approximately 50° C. with an ending pH of 8.49. After filtration, the wet cake was washed with de-ionized water (4×300 mL) at 50° C. while pH became 7.51, followed by another optional wash with water (1×300 mL). The catalyst cake was then dried at approximately 110° C. under vacuum for 10 hours to provide the dried 1 wt. % Pt/C catalyst (14.8 g).

B. Method Ib (No $NaBH_4$ Reduction)

Activated carbon (15.7 g) was suspended to form a slurry in de-ionized water (approx. 140 mL) with stirring for about 20 minutes. The pH of the resulting slurry was pH 7.78. A solution of $H_2PtCl_6 \cdot 6H_2O$ (0.41 g) in de-ionized water (approx. 15 mL) was added dropwise to the carbon slurry over a period of about 17 minutes. The pH of the resulting slurry dropped to pH 3.67 upon the completion of addition of the platinum solution. The resulting slurry was stirred for another 28 minutes at ambient temperature and the pH rose to about pH 4.25. The slurry was then heated to 60° C. over approximately 30 minutes while the pH was maintained at about pH 4.00 by addition of 1 M NaOH solution. Upon reaching the temperature of 60° C., the pH of the slurry was increased by an increment of 0.5 every 5 minutes with addition of 1 M NaOH solution until about pH 6.00. The stirring of the slurry was continued for 10 minutes at 60° C. and pH 6.0. The solution was then cooled to approximately 50° C. and the solution had pH 6.08. The pH of the slurry rose gradually to 7.65 while it continued to cool to approximately 43° C. It was then heated to approximately 55° C. in 14 minutes with an ending pH of 8.99. After filtration, the wet cake was washed with de-ionized water (4×300 mL) at 50° C. The catalyst cake was then dried at approximately 110° C. under vacuum for 10 hours to provide the dried 1 wt. % Pt/C catalyst (15.3 g).

C. Method II

Activated carbon (15.7 g) was suspended to form a slurry in de-ionized water (approximately 120 mL) with stirring for about 40 minutes. The pH of the resulting slurry was adjusted to pH 8.33 by addition of 1M NaOH solution. A solution of $H_2PtCl_6 \cdot 6H_2O$ (0.40 g) in de-ionized water (approximately 10 mL) was added dropwise to the carbon slurry over a period of about 8 minutes. The pH of the resulting slurry dropped to pH 3.60 upon the completion of addition of the platinum solution. The resulting slurry was stirred for another 10 minutes at ambient temperature and the pH rose to pH 4.05. The pH was then adjusted to about pH 5.0 with 1M NaOH and the resulting solution was stirred for another 8 minutes. The slurry was then heated to 60° C. over about 15 minutes while the pH was maintained at about pH 5.0 by addition of 1 M NaOH solution. Upon reaching the temperature of 60° C. for 5 minutes, the pH of the slurry was increased to about pH 6.0 with addition of 1 M NaOH solution and was maintained for 10 minutes. The pH of the slurry was increased again to about pH 6.5 and was maintained for another 10 minutes. The resulting slurry was then cooled to below about 50° C. in about 10 minutes. A solution of $NaBH_4$ in 14 M NaOH (12 wt. %, 0.50 g) was diluted to 5 mL with de-ionized water; and the diluted solution was added dropwise to the aforementioned prepared slurry over 5 minutes. The stirring was continued for another 5 minutes after the addition, and the resulting pH of the slurry rose to pH 8.41. The slurry was then heated to about 57° C. over about 10 minutes with an ending pH of 9.16. After filtration, the wet cake was washed with de-ionized water (4×350 mL) at 50° C. with a final pH of 6.03. The catalyst cake was then dried at about 110° C. under vacuum for 10 hours to provide the dried 1 wt. % Pt/C catalyst (15.3 g).

D. Method III

Activated carbon (15.5 g) was suspended to form slurry in de-ionized water (approximately 120 mL) with stirring for about 45 minutes. The pH of the resulting slurry was adjusted to pH 9.00 by addition of 1M NaOH solution. A solution of $H_2PtCl_6 \cdot 6H_2O$ (0.41 g) in de-ionized water (approximately 10 mL) was added dropwise to the carbon slurry over a period of about 8.5 minutes. The pH of the resulting slurry dropped to pH 3.99 upon the completion of addition of the platinum solution. The resulting slurry was stirred for another 20 minutes at ambient temperature and the pH rose to pH 4.77. The pH was then adjusted to about pH 5.0 with 1M NaOH. The slurry was then heated to 60° C. over about 15 minutes while the pH was maintained at about pH 5.0 by addition of 1 M NaOH solution. Upon reaching the temperature of 60° C. for 5 minutes, the pH of the slurry was increased to about pH 6.0 with addition of 1 M NaOH solution and was maintained for 10 minutes. The pH of the slurry was increased again to about pH 6.5 and was maintained for another 10 minutes. The resulting slurry was then cooled to below about 50° C. in about 15 minutes. A solution of $NaBH_4$ in 14 M NaOH (12 wt. %, 0.52 g) was diluted to 5 mL with de-ionized water; and the diluted solution was added dropwise to the aforementioned prepared slurry over 5 minutes. The stirring was continued for another 5 minutes after the addition, and the resulting pH of the slurry rose to pH 8.14. The slurry was then heated to about 55° C. over about 10 minutes with an ending pH of 8.94. After filtration, the wet cake was washed with de-ionized water (4×350 mL) at 50° C. with a final pH of 6.38. The catalyst cake was then dried at about 110° C. under vacuum for 10 hours to provide the dried 1 wt. % Pt/C catalyst (15.2 g).

E. Method IV

Activated carbon (15.6 g) was suspended to form a slurry in de-ionized water (approximately 110 mL) with stirring for about 27 minutes. The pH of the resulting slurry was adjusted to pH 8.50 by addition of 1M NaOH solution. A solution of $H_2PtCl_6 \cdot 6H_2O$ (0.41 g) in de-ionized water (approximately 10 mL) was added dropwise to the carbon slurry over a period of about 12 minutes with co-addition of 1M NaOH. The pH of the resulting slurry dropped to pH 4.57 upon the completion of addition of the platinum solution. The resulting slurry was stirred for another 30 minutes at ambient temperature and the pH rose to pH 5.12. The slurry was then heated to 60° C. over about 14 minutes while the pH dropped to pH 4.11. Upon reaching the temperature of 60° C., the pH of the slurry was maintained at about pH 4.1 for 15 minutes with addition of 1 M NaOH solution. Subsequently, the pH was increase to about pH 4.5 and was maintained for another 10 minutes. The pH of the slurry was increased by an increment of 0.5 every 10 minutes with addition of 1 M NaOH solution until about pH 6.0. The stirring of the slurry was continued for 10 minutes at 60° C. and pH 6.0, and then cooled to about 45° C. in about 15 minutes. A solution of $NaBH_4$ in 14 M NaOH (12 wt. %, 0.80 g) was diluted to 8 mL with deionized water; and the diluted solution was added dropwise to the aforementioned prepared slurry over 8 minutes. The stirring was continued for another 12 minutes after the addition, and the resulting pH of the slurry rose to pH 8.00 with a temperature of 37° C. The slurry was then heated to about 55° C. over about 16 minutes with an ending pH of 8.81. After filtration, the wet cake was washed with de-ionized water (4×350 mL) at 50° C. with a final pH of 6.40. The catalyst cake was then dried at about 110° C. under vacuum for 10 hours to provide the dried 1 wt. % Pt/C catalyst (15.2 g).

F. Method V

Activated carbon (15.6 g) was suspended to form a slurry in de-ionized water (approximately 110 mL) with stirring while the slurry was heated to 41° C. for about 20 minutes. The pH of the resulting slurry was adjusted to pH 9.00 by addition of 1M NaOH solution. A solution of $H_2PtCl_6.6H_2O$ (0.41 g) in de-ionized water (approximately 10 mL) was added dropwise to the carbon slurry over a period of about 11 minutes with co-addition of 1M NaOH while maintaining the pH of the slurry to above 6.0 and the temperature at about 41° C. The slurry was then stirred for another 20 minutes at about 41° C. and the pH of slurry was maintained at pH 6.1 with co-addition of 1M NaOH if necessary. The slurry was then heated to about 70° C. over a period of about 20 minutes while the pH was maintained between pH 6.1 to pH 6.2 with 1M NaOH. Upon reaching 70° C., the pH of the slurry was raised to pH 7.0 with 1M NaOH solution and maintained for 10 minutes. After the slurry was cooled below 50° C. in about 17 minutes, a solution of $NaBH_4$ in 14 M NaOH (12 wt. %, 1.00 g) diluted in de-ionized water (10 mL) was added dropwise over 8 minutes. The stirring was continued for another 10 minutes after the addition, and the resulting pH of the slurry rose to pH 9.52 with a temperature of about 42° C. The slurry was then heated to about 60° C. in about 10 minutes with an ending pH of 9.78. After filtration, the wet cake was washed with de-ionized water (4×350 mL) at 55° C. with a final pH of 7.90. The catalyst cake was then dried at about 110° C. under vacuum for 10 hours to provide the dried 1 wt. % Pt/C catalyst (15.2 g).

G. Method VI

Activated carbon (15.7 g) was suspended to form a slurry in de-ionized water (approximately 110 mL) with stirring for about 45 minutes. The pH of the resulting slurry was adjusted to about pH 6.50 by addition of 1M HCl solution. A solution of $H_2PtCl_6.6H_2O$ (0.40 g) in de-ionized water (approximately 10 mL) was added dropwise to the carbon slurry over a period of about 11 minutes at ambient temperature. The pH of the resulting slurry dropped to pH 3.27 upon the completion of addition of the platinum solution. The resulting slurry was stirred for another 22 minutes at ambient temperature and the pH rose to pH 3.65. The pH was adjusted to pH 3.28 with 1 M HCl solution. The slurry was then stirred for another 18 minutes and the pH of slurry ended at pH 3.54. The slurry was then heated to about 60° C. over a period of about 15 minutes while the pH dropped to pH 3.13. Upon reaching 60° C., the pH of the slurry was raised to about pH 3.5 with 1M NaOH solution and maintained for 10 minutes. The pH of the slurry was increased by an increment of 0.5 every 5 minutes with addition of 1 M NaOH solution until about pH 6.0. The stirring of the slurry was continued for 10 minutes at 60° C. and pH 6.0, and then cooled to below about 50° C. A solution of $NaBH_4$ in 14 M NaOH (12 wt. %, 0.56 g) diluted in de-ionized water (4.5 mL) was added dropwise over 6 minutes. The stirring was continued for another 10 minutes after the addition, and the resulting pH of the slurry rose to pH 7.95 with a temperature of about 42° C. The slurry was then heated to about 52° C. in about 10 minutes with an ending pH of 8.64. After filtration, the wet cake was washed with de-ionized water (3×300 mL at about 50° C., final 1×300 mL at ambient temperature) with a final pH of 7.30. The catalyst cake was then dried at about 110° C. under vacuum for 10 hours to provide the dried 1 wt. % Pt/C catalyst (15.2 g).

H. Method VII

Activated carbon (15.7 g) was suspended to form a slurry in de-ionized water (approx. 110 mL) with stirring for about 30 minutes. The pH of the resulting slurry was pH 7.73. A solution of $H_2PtCl_6.6H_2O$ (0.40 g) in de-ionized water (approx. 10 mL) was added dropwise to the carbon slurry over a period of about 15 minutes. The pH of the resulting slurry dropped to pH 3.48 upon the completion of addition of the platinum solution. The resulting slurry was stirred for another 35 minutes at ambient temperature and the pH of slurry rose to pH 4.03. The slurry was then heated to 60° C. over approximately 20 minutes while the pH was maintained at about pH 4.00 by addition of 1 M NaOH solution. Upon reaching the temperature of 60° C., the pH of the slurry was increased by an increment of 0.5 every 5 minutes with addition of 1 M NaOH solution until about pH 6.00. The stirring of the slurry was continued for 10 minutes at 60° C. and pH 6.0. The pH of the slurry was increased again to about pH 6.5 and was maintained for another 15 minutes, and then cooled to below approximately 50° C. A solution of $NaBH_4$ in 14 M NaOH (12 wt. %, 0.60 g) was diluted to 10 mL with de-ionized water; and the diluted solution was added dropwise to the aforementioned prepared slurry over 15 minutes. Upon completion of addition, the slurry was heated to approximately 52° C. with an ending pH of 8.94. After filtration, the wet cake was washed with de-ionized water (3×300 mL at about 50° C., final 1×300 mL at ambient temperature) with a final pH of 7.45. The catalyst cake was then dried at approximately 110° C. under vacuum for 10 hours to provide the dried 1 wt. % Pt/C catalyst (15.3 g).

I. Method VIIIa

Activated carbon (15.7 g) was suspended to form a slurry in de-ionized water (approximately 110 mL) containing 1,4-cyclohexanedimethanol (CHDM) (1.19 g) with stirring while the slurry was heated to 45° C. for about 40 minutes. The pH of the resulting slurry was adjusted to pH 7.45 by addition of 1M NaOH solution. A solution of $H_2PtCl_6.6H_2O$ (0.41 g) in de-ionized water (approx. 10 mL) was added dropwise to the carbon slurry over a period of about 13 minutes at the temperature of about 43° C. to 44° C. The pH of the resulting slurry dropped to pH 3.06 upon the completion of addition of the platinum solution. The pH of slurry was adjusted to pH 3.50 and the resulting slurry was stirred for 5 minutes at about 43° C. The pH of slurry was raised to pH 4.00 and the resulting slurry was stirred for another 15 minutes at about 43° C. The slurry was then heated to 60° C. over approximately 10 minutes while the pH was maintained at about pH 4.00 by addition of 1 M NaOH solution. Upon reaching the temperature of 60° C., the pH of the slurry was increased by an increment of 0.5 every 5 minutes with addition of 1 M NaOH solution until about pH 6.00. The stirring of the slurry was continued for 10 minutes at 60° C. and pH 6.0. The pH of the slurry was increased again to about pH 6.5 and was maintained for another 15 minutes, and then cooled to below approximately 50° C. A solution of $NaBH_4$ in 14 M NaOH (12 wt. %, 0.60 g) was diluted to 10 mL with deionized water; and the diluted solution was added dropwise to the aforementioned prepared slurry over 16 minutes. Upon completion of addition, the slurry was heated to approximately 56° C. with an ending pH of 8.76. After filtration, the wet cake was washed with de-ionized water (3×300 mL at about 55° C., final 1×300 mL at ambient temperature). The catalyst cake was then dried at approximately 110° C. under vacuum for 10 hours to provide the dried 1 wt. % Pt/C catalyst (16.2 g).

J. Method VIIIb

Activated carbon (15.7 g) was suspended to form a slurry in de-ionized water (approximately 110 mL) containing 1,4-cyclohexanedimethanol (CHDM) (2.44 g) with stirring while the slurry was heated to 70° C. for about 30 minutes. The pH of the resulting slurry was adjusted to pH 6.95 by addition of 1M NaOH solution while the slurry was cooling back to 41° C. A solution of $H_2PtCl_6.6H_2O$ (0.41 g) in de-ionized water (approx. 10 mL), pre-adjusted to about pH 1.4 with 1M NaOH solution (about 10 drops), was added dropwise to the carbon slurry over a period of about 14 minutes at the temperature of about 41° C. to 42° C. The pH of the resulting slurry dropped to pH 3.60 upon the completion of addition of the platinum solution, and the slurry was then continued to stir for 6 more minutes. The pH of slurry was adjusted to pH 4.50 and the resulting slurry was stirred for 5 minutes at about 41° C. The pH of slurry was raised to pH 5.50. The slurry was then heated to 60° C. over approximately 10 minutes while the pH was maintained at about pH 5.50 by addition of 1 M NaOH solution. Upon reaching the temperature of 60° C., the pH of the slurry was increased to about pH 6.50. The stirring of the slurry was continued for 15 minutes at 60-62° C. and pH 6.50, and then the solution was cooled to below approximately 50° C. A solution of $NaBH_4$ in 14 M NaOH (12 wt. %, 0.60 g) was diluted to 10 mL with de-ionized water; and the diluted solution was added dropwise to the aforementioned prepared slurry over 11 minutes. Upon completion of addition, the solution was continued for stirring for 10 minutes, and then heated to approximately 53° C. over 10 minutes with an ending pH of 8.80. After filtration, the wet cake was washed with de-ionized water (3×300 mL at about 50° C.). The catalyst cake was then dried at approximately 110° C. under vacuum for 10 hours to provide the dried 1 wt. % Pt/C catalyst (17.1 g).

K. Method IX

Activated carbon (15.7 g) was suspended to form a slurry in de-ionized water (approximately 110 mL) containing sucrose (1.20 g) with stirring while the slurry was heated to 45° C. for about 30 minutes. The pH of the resulting slurry was adjusted to pH 7.63 by addition of 1M NaOH solution. A solution of $H_2PtCl_6.6H_2O$ (0.41 g) in de-ionized water (approx. 10 mL) was added dropwise to the carbon slurry over a period of about 13 minutes at the temperature of about 43° C. to 44° C. The pH of the resulting slurry dropped to pH 3.45 upon the completion of addition of the platinum solution. At about 44° C., the pH of slurry was adjusted to pH 3.50 with stirring for 5 minutes and was then increased by an increment of 0.5 every 10 minutes until about pH 4.50. The slurry was then heated to 60° C. over approximately 13 minutes while the pH was maintained at about pH 4.50 by addition of 1 M NaOH solution. Upon reaching the temperature of 60° C., the pH of the slurry was increased to about pH 5.00 for 7 minutes, to pH 5.50 for 5 minutes, pH 6.00 for 10 minutes, and to pH 6.50. The stirring of the slurry was continued for 15 minutes at pH 6.50, and then the solution was cooled to below approximately 50° C. A solution of $NaBH_4$ in 14 M NaOH (12 wt. %, 0.60 g) was diluted to 10 mL with deionized water; and the diluted solution was added dropwise to the aforementioned prepared slurry over 12 minutes. Upon completion of addition, the solution was continued for stirring for 10 minutes, and then heated to approximately 56° C. over 12 minutes with an ending pH of 9.10. After filtration, the wet cake was washed with de-ionized water (3×300 mL at about 50° C., final 1×300 mL at ambient temperature). The catalyst cake was then dried at approximately 110° C. under vacuum for 10 hours to provide the dried 1 wt. % Pt/C catalyst (16.2 g).

L. Method Xa

Activated carbon (15.6 g) was suspended to form a slurry in de-ionized water (approximately 110 mL) with stirring for about 27 minutes. The pH of the resulting slurry was adjusted to pH 8.20 by addition of 1M NaOH solution. A solution of $H_2PtCl_6.6H_2O$ (0.41 g) in de-ionized water (approx. 10 mL), pre-adjusted to about pH 11.4 with 1M NaOH solution (1.60 g), was added dropwise to the carbon slurry over a period of about 18 minutes at ambient temperature. The pH of the resulting slurry dropped to pH 7.69 upon the completion of addition of the platinum solution, and the slurry was then continued to stir for 18 minutes. The pH of slurry was adjusted from pH 7.17 to pH 8.00 at about 28° C. and stirred for 2 minutes. The slurry was then heated to 60° C. over approximately 12 minutes while the pH was maintained at about pH 8.00 by addition of 1 M NaOH solution. Upon reaching the temperature of 60° C., the stirring of the slurry was continued for 15 minutes, and then the solution was cooled to below approximately 50° C. A solution of $NaBH_4$ in 14 M NaOH (12 wt. %, 0.60 g) was diluted to 10 mL with de-ionized water; and the diluted solution was added dropwise to the aforementioned prepared slurry over 11 minutes. Upon completion of addition, the solution was continued for stirring for 10 minutes, and then heated to approximately 54° C. over 10 minutes with an ending pH of 9.54. After filtration, the wet cake was washed with de-ionized water (3×300 mL at about 50° C.). The catalyst cake was then dried at approximately 110° C. under vacuum for 10 hours to provide the dried 1 wt. % Pt/C catalyst (15.0 g).

M. Method Xb

Activated carbon (15.7 g) was suspended to form a slurry in de-ionized water (approximately 110 mL) with stirring while the slurry was heated to 44° C. for about 34 minutes. The pH of the resulting slurry was adjusted to pH 8.34 by addition of 1M NaOH solution. A solution of $H_2PtCl_6.6H_2O$ (0.41 g) in de-ionized water (approx. 10 mL) was pre-adjusted to about pH 11.8 with 1M NaOH solution (1.79 g). The resulting platinic acid solution was added dropwise to the carbon slurry over a period of about 20 minutes at the temperature of 44-45° C. while the pH of the slurry was maintained at approximately pH 8.0 with 1M NaOH solution. The pH of the resulting slurry ended with pH 8.06 upon the completion of addition of the platinum solution, and the slurry was then continued to stir for 20 minutes at pH 8.00. The slurry was then heated to 60° C. over approximately 10 minutes while the pH was maintained at about pH 8.00 by addition of 1 M NaOH solution. Upon reaching the temperature of 60° C., the stirring of the slurry was continued for 20 minutes, and then the solution was cooled to below approximately 50° C. A solution of $NaBH_4$ in 14 M NaOH (12 wt. %, 0.60 g) was diluted to 10 mL with de-ionized water; and the diluted solution was added dropwise to the aforementioned prepared slurry over 10 minutes. Upon completion of addition, the solution was continued for stirring for 10 minutes, and then heated to approximately 54° C. over 10 minutes with an ending pH of 9.61. After filtration, the wet cake was washed with de-ionized water (3×300 mL at about 50° C.). The catalyst cake was then dried at approximately 110° C. under vacuum for 10 hours to provide the dried 1 wt. % Pt/C catalyst (15.2 g).

Parameters for the process are summarized in Table 5-A and Table 5-B.

TABLE 5-A

Parameters for the Preparation of 1% Pt Catalyst (Method Ia to VII) on activated carbon

| Conditions | Method Ia | Method II | Method III | Method IV | Method V | Method VI | Method VII |
|---|---|---|---|---|---|---|---|
| Amount of carbon (g) | 15.0 | 15.7 | 15.5 | 15.6 | 15.6 | 15.7 | 15.7 |
| Initial Carbon Slurry concentration (g/mL) | ~0.10 | ~0.13 | ~0.13 | ~0.14 | ~0.14 at 41° C. | ~0.14 | ~0.14 |
| pH of initial slurry | 8.48 | 8.33 | 9.00 | 8.50 | 9.00 | 6.50 | 7.73 |
| Amount of $H_2PtCl_6 \cdot 6H_2O$ (g) | 0.40 | 0.40 | 0.41 | 0.41 | 0.41 | 0.40 | 0.40 |
| pH after addition of $H_2PtCl_6 \cdot 6H_2O$ | 5.17 | 3.60 | 3.99 | 4.57 | 6.0 at 41° C. | 3.27 | 3.48 |
| Temperature of the first heating | 60° C. | 60° C. | 60° C. | 60° C. | 70° C. | 60° C. | 60° C. |
| pH range during the first heating | 4.50 to 6.0 | 5.0 to 6.5 | 5.0 to 6.5 | 4.1 to 6.0 | 6.1 to 7.0 | 3.1 to 6.0 | 4.0 to 6.5 |
| Temperature before adding reducing agent | <50° C. | <50° C. | <50° C. | ~45° C. | <50° C. | <50° C. | <50° C. |
| Amount of Reducing Agent (12 wt. % $NaBH_4$ in 14M NaOH) (g) | 0.50 | 0.50 | 0.52 | 0.80 | 1.00 | 0.56 | 0.60 |
| pH after adding $NaBH_4$ | 7.59 | 8.41 | 8.14 | 8.00 | 9.52 | 7.95 | 8.51 |
| Temperature of the second heating | 50° C. | 57° C. | 55° C. | 55° C. | 55° C. | 52° C. | 52° C. |
| Ending pH after the $2^{nd}$ heating | 8.49 | 9.16 | 8.94 | 8.81 | 9.78 | 8.64 | 8.94 |
| pH after water wash (4 x) of wet cake | 7.51 | 6.03 | 6.38 | 6.40 | 7.90 | 7.30 | 7.45 |

TABLE 5-B

Parameters for the Preparation of 1% Pt Catalyst (Method VIIIa to Xb, Ib) on activated carbon

| Conditions | Method VIIIa | Method VIIIb | Method IX | Method Xa | Method Xb | Method Ib |
|---|---|---|---|---|---|---|
| Amount of carbon (g) | 15.7 | 15.7 | 15.7 | 15.6 | 15.7 | 15.0 |
| Initial Carbon Slurry concentration (g/mL) | ~0.14 at 45° C. | ~0.14 at 70° C. | ~0.14 at 45° C. | ~0.14 | ~0.14 at 45° C. | ~0.11 |
| Pore blocking modifier | CHDM (1.19 g) | CHDM (2.44 g) | Sucrose (1.20 g) | none | none | none |
| pH of initial slurry | 7.45 | 6.95 at 41° C. | 7.63 | 8.20 | 8.34 | 7.78 |
| Amount of $H_2PtCl_6 \cdot 6H_2O$ (g) | 0.41 | 0.41 | 0.41 | 0.41 | 0.41 | 0.41 |
| pH adjustment of the $H_2PtCl_6 \cdot 6H_2O$ solution | none | pH 1.4 | none | pH 11.4 | pH 11.8 | none |
| pH after addition of $H_2PtCl_6 \cdot 6H_2O$ | 3.06 | 3.60 | 3.45 | 7.69 | 8.00 | 3.67 |
| Temperature of the first heating | 60° C. | 60° C. | 60° C. | 60° C. | 60° C. | 60° C. |
| pH range during the first heating | 4.0 to 6.5 | 5.5 to 6.5 | 4.5 to 6.5 | 8.0 | 8.0 | 4.0 to 6.0 |
| Temperature before adding reducing agent | <50° C. | <50° C. | <50° C. | <50° C. | <50° C. | <50° C. |
| Amount of Reducing Agent (12 wt. % $NaBH_4$ in 14M NaOH) (g) | 0.60 | 0.60 | 0.60 | 0.60 | 0.60 | None |
| Temperature of the second heating | 56° C. | 53° C. | 56° C. | 54° C. | 54° C. | 55° C. |
| Ending pH after the $2^{nd}$ heating | 8.76 | 8.80 | 9.10 | 9.54 | 9.61 | 8.99 |

Example 8: Long-term Cycle Study of 1 wt. % Pt on Activated Carbon Support

Example 2 was repeated using 1 wt. % Pt/C catalysts over a series of reaction cycles (e.g., over 30 or 40 cycles). The first catalyst was a commercial Pt/C catalyst that was calcined at 800° C. The second catalyst was also a Pt/C catalyst that was calcined at 800° C. However, the second catalyst was prepared according to procedure Method Ia in Example 7. In each run of the hydrogenation reaction, approximately 755 mg (dry basis) of each catalyst and 150 g of a 30 wt. % 2,5-dichloronitrobenzene in acetic acid were loaded into the reactor. Hydrogen was charged to the reactor at a pressure of 687 kPa (85 psig). The reactor was heated to a temperature of 45° C. The results of these runs over the course of a series of reaction cycle are provided in Table 6.

TABLE 6

Cycles vs. Dechlorination

| | Commercial 1 wt. % Pt/C | | | | Prepared 1 wt. % Pt/C | | | |
|---|---|---|---|---|---|---|---|---|
| # of Cycle | 2-CA + 3-CA (mol. %) | 2-CA (mol. %) | 3-CA/2-CA ratio | Reaction time (min) | 2-CA + 3-CA (mol. %) | 2-CA (mol. %) | 3-CA/2-CA ratio | Reaction time (min) |
| 1  | 0.25 | 0.057 | 3.40 | 44 | 0.13 | 0.032 | 2.97 | 53 |
| 2  | 0.22 | 0.049 | 3.52 | 53 | 0.11 | 0.025 | 3.34 | 48 |
| 5  | 0.23 | 0.064 | 2.60 | 45 | 0.11 | 0.027 | 3.27 | 47 |
| 8  | 0.23 | 0.062 | 2.70 | 48 | 0.15 | 0.039 | 2.91 | 44 |
| 12 | 0.24 | 0.072 | 2.35 | 50 | 0.13 | 0.035 | 2.71 | 47 |
| 16 | 0.23 | 0.067 | 2.43 | 50 | —    | —     | —    | 49 |
| 17 | —    | —     | —    | 51 | 0.13 | 0.040 | 2.20 | 49 |
| 18 | —    | —     | —    | 52 | 0.13 | 0.040 | 2.16 | 48 |
| 19 | —    | —     | —    | 51 | 0.13 | 0.040 | 2.16 | 44 |
| 21 | 0.16 | 0.050 | 2.18 | 52 | —    | —     | —    | 47 |
| 27 | 0.13 | 0.039 | 2.31 | 57 | 0.10 | 0.035 | 1.89 | 52 |
| 28 | —    | —     | —    | 57 | 0.10 | 0.032 | 2.01 | 50 |
| 33 | —    | —     | —    | —  | 0.10 | 0.033 | 1.76 | 52 |
| 34 | —    | —     | —    | —  | 0.09 | 0.033 | 1.74 | 52 |
| 39 | —    | —     | —    | —  | 0.09 | 0.033 | 1.64 | 55 |
| 43 | —    | —     | —    | —  | 0.08 | 0.032 | 1.63 | 55 |

Both catalysts exhibited good stability after long-term usages. The results confirm that the higher selectivity to the preferred dechlorination compound 2-chloroaniline was observed over the series of cycles on both catalysts. These results are consistent with those presented in Example 6.

Example 9: Long-term Cycle Study of 1 wt. % Pt on Activated Carbon Support

Figure 6:
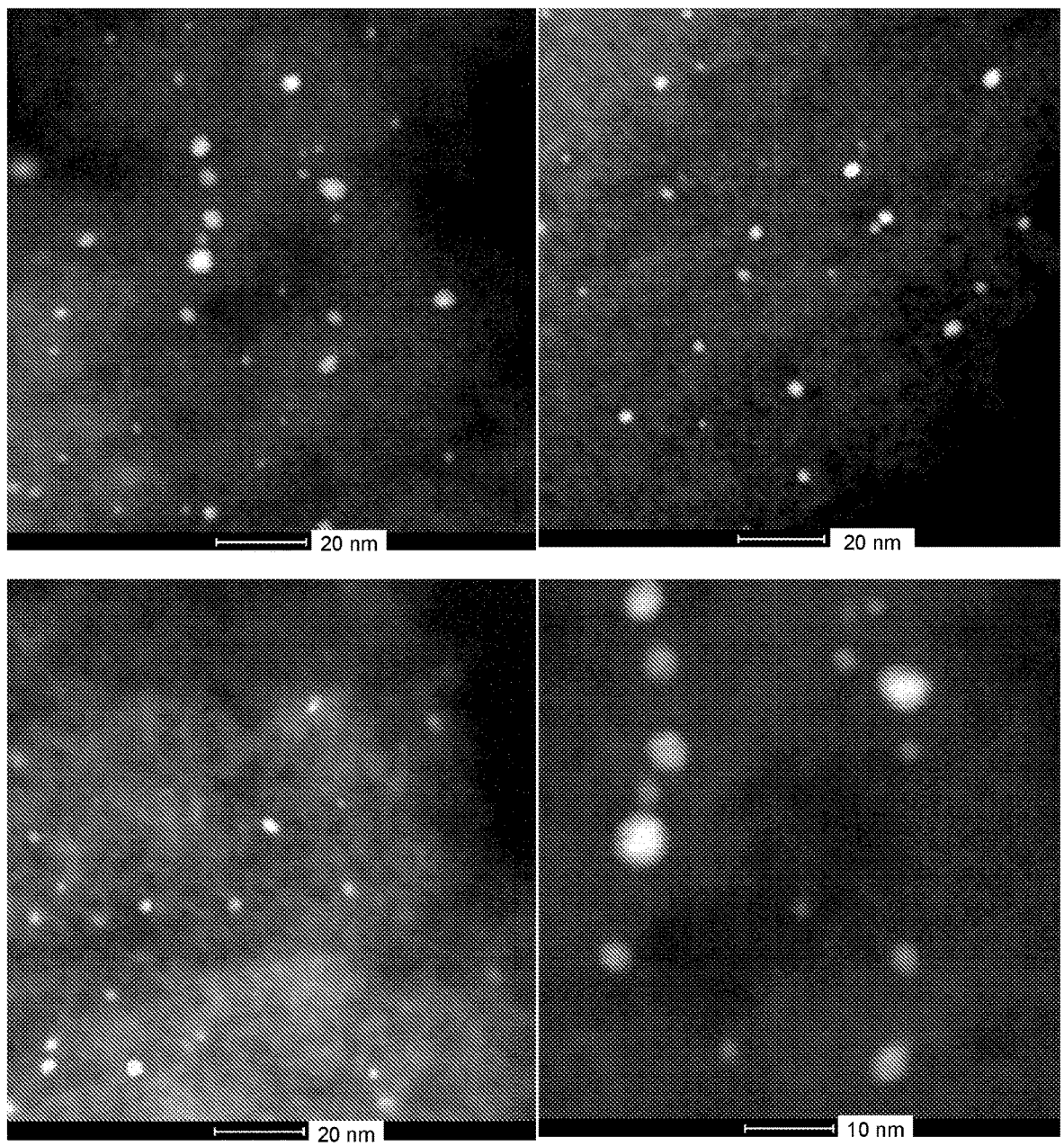
FIG. 6 presents a series of STEM images of the surface of a prepared platinum on carbon catalyst after calcination.
Figure 7:
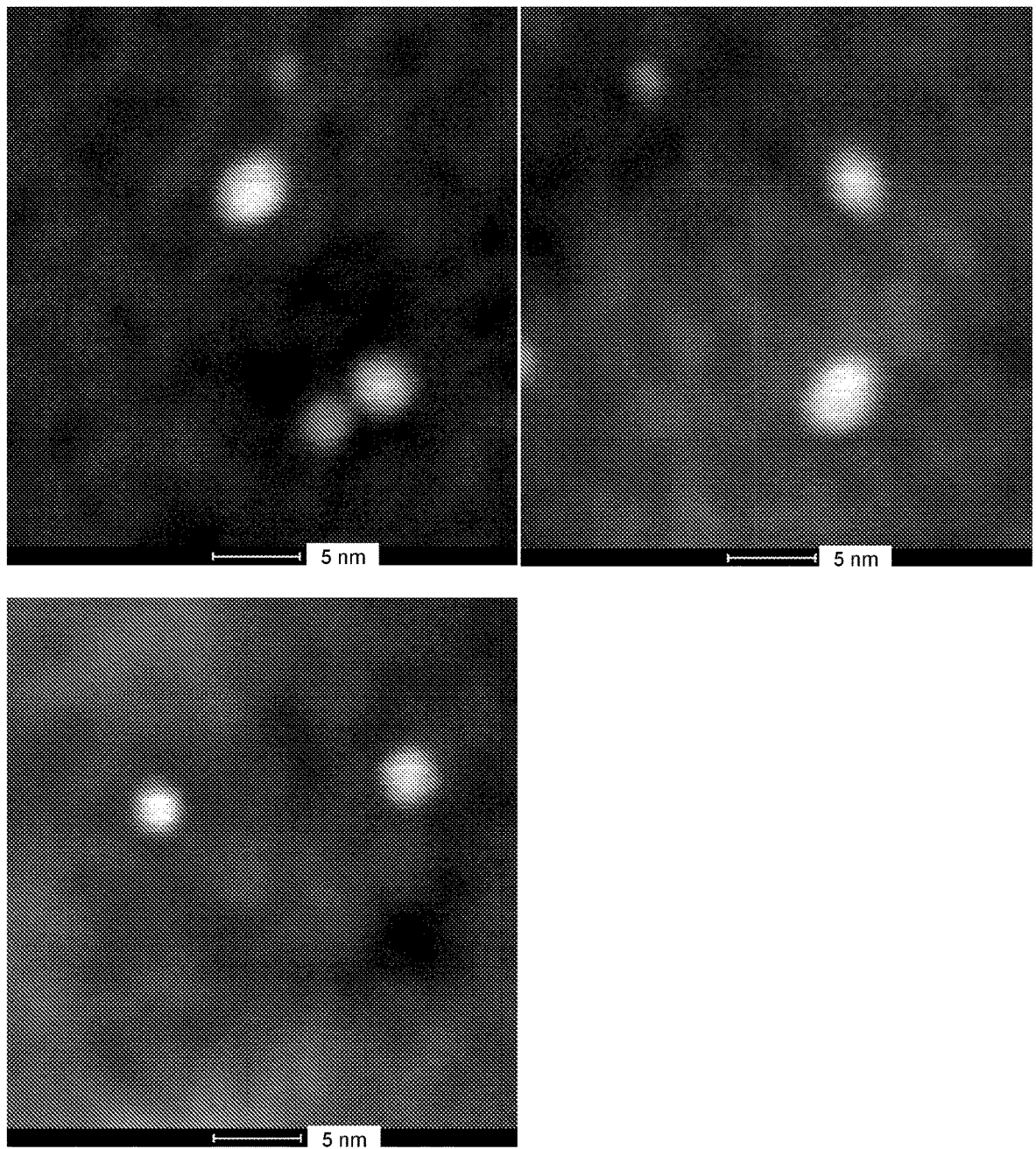
FIG. 7 presents a series of STEM images of the surface of a prepared platinum on carbon catalyst after calcination.
Figure 8:
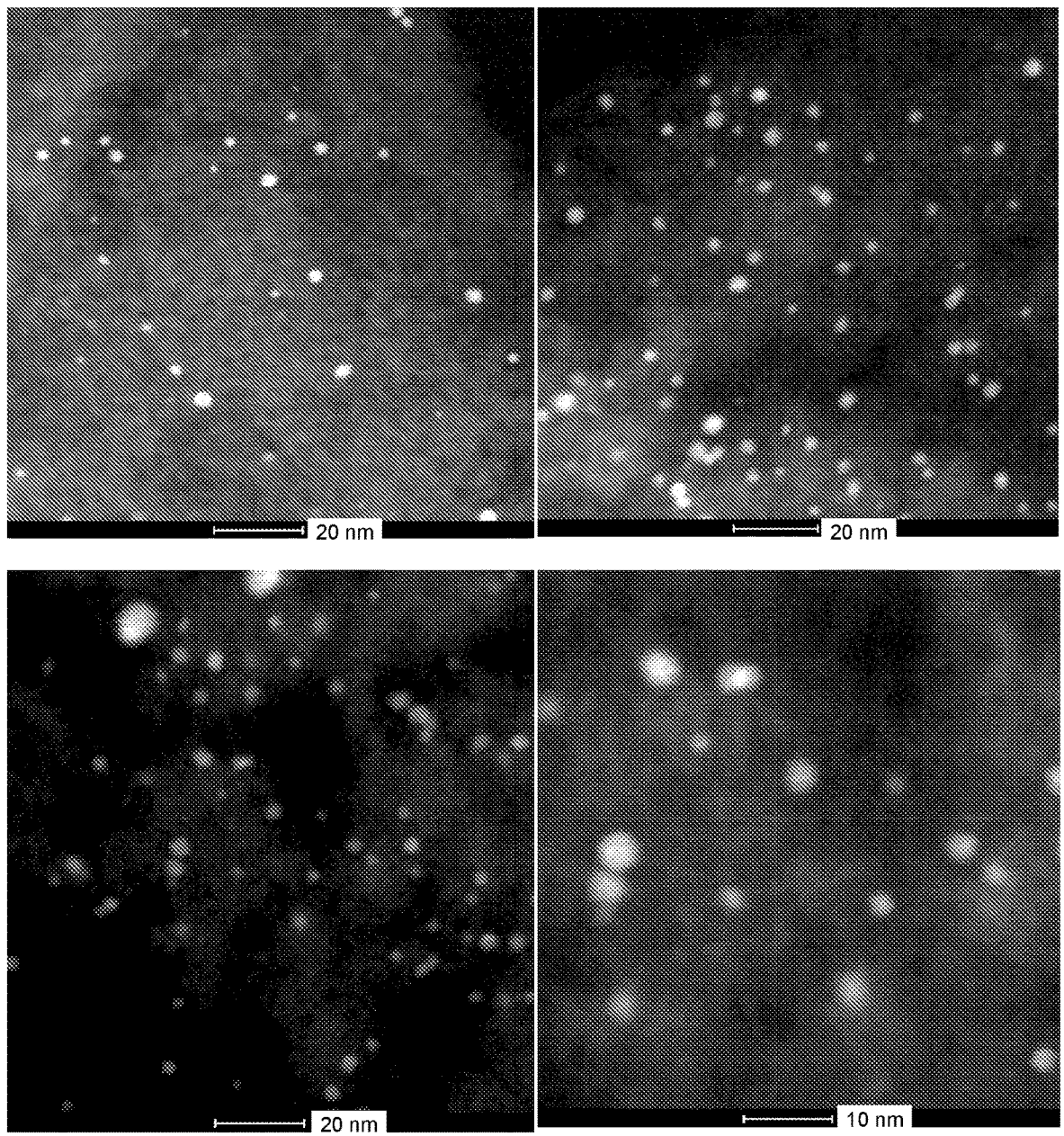
FIG. 8 presents a series of STEM images of the surface of a prepared platinum on carbon catalyst after calcination and after use in 43 hydrogenation reaction cycles.
Figure 9:
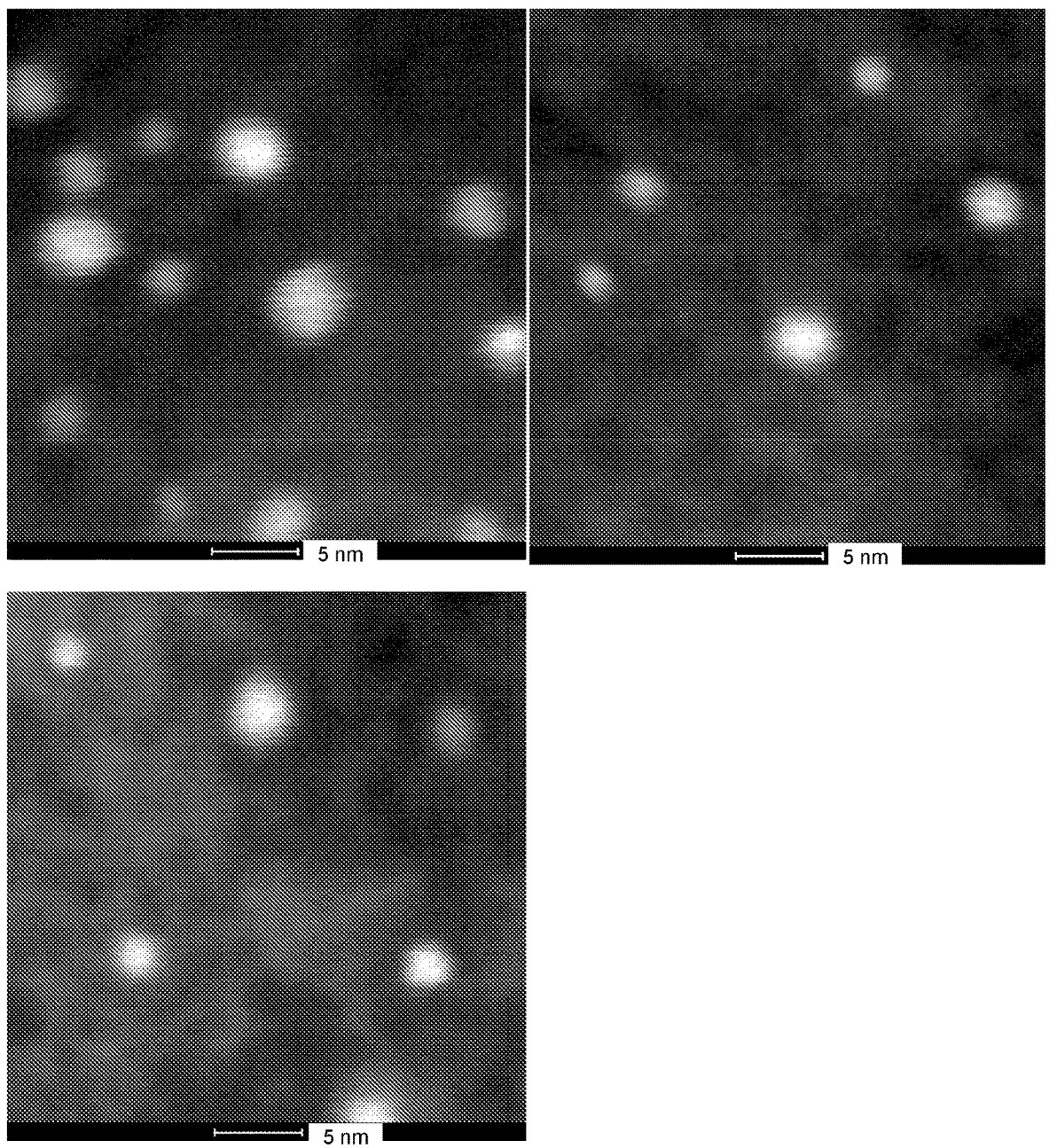
FIG. 9 presents a series of STEM images of the surface of a prepared platinum on carbon catalyst after calcination and after use in 43 hydrogenation reaction cycles.

The catalyst surface of the prepared catalyst from Example 8 was imaged after the calcination and after use in 43 cycles of the hydrogenation reaction using STEM. FIGS. 6 and 7 present a series of images for the catalyst surface after calcination. FIGS. 8 and 9 present a series of images for the catalyst surface after 43 cycles of the hydrogenation reaction. These images show that the catalyst is stable (e.g., resistant to leaching) over the course of numerous reaction cycles.

Example 10: Analysis of Activated Carbon Supports

The activated carbon supports used for the 1 wt. % Pt/C catalyst in Example 9 and the 5 wt. % Pt/C in Example 6 were analyzed for physical properties such as surface area using the Langmuir nitrogen absorption method. The results of the analysis are provided in Table 7. The micropore surface area is attributable to pores that are less than 2 nm. The external surface area is attributable to pores that are greater than 2 nm.

TABLE 7

Physical Properties of Activated Carbon Supports for Selected Catalysts

| Carbon Type | Total Langmuir Surface Area ($m^2/g$) | Micropore Surface Area ($m^2/g$) | External Surface Area ($m^2/g$) | Average pore diameter (nm) |
|---|---|---|---|---|
| A[1] | 2704 | 1944 | 760 | 2.3 |
| B[2] | 1597 | 1294 | 303 | 2.0 |

[1]The activated carbon support used for the 1 wt. % Pt/C catalyst in Example 9.
[2]The activated carbon support used for the 5 wt. % Pt/0.5 wt. % Fe/C catalyst in Example 6.

Example 11: Effect of Hydrogen Pressure with Calcined Platinum Catalyst

Example 2 was repeated with a 1 wt. % Pt/C catalyst that was calcined at 800° C. In this run, the hydrogen pressure was increased from 687 kPa (85 psig) in reaction cycles 1 to 33 to 963 kPa (125 psig) in reaction cycles 34 to 40 while using the same bed of catalyst. A 2,5-dichloronitrobenzene solution in acetic acid (30 wt. %) and a reaction temperature of 45° C. were used. The results of this experiment at different cycles are provided in Table 8.

TABLE 8

Hydrogen Pressure vs. Dechlorination with Calcined Platinum Catalyst

| | | 1 wt. % Pt/C | | | |
|---|---|---|---|---|---|
| # of Cycle | Hydrogen Pressure | 2-CA + 3-CA (mol. %) | 2-CA (mol. %) | 3-CA/2-CA ratio | Reaction time (min) |
| 1  | 687 kPa    | 0.25 | 0.057 | 3.40 | 44 |
| 2  | (85 psig)  | 0.22 | 0.049 | 3.52 | 53 |
| 5  |            | 0.23 | 0.064 | 2.60 | 45 |
| 8  |            | 0.23 | 0.062 | 2.70 | 48 |
| 12 |            | 0.24 | 0.072 | 2.35 | 50 |
| 16 |            | 0.23 | 0.067 | 2.43 | 50 |
| 17 |            | —    | —     | —    | 51 |
| 18 |            | —    | —     | —    | 52 |

TABLE 8-continued

Hydrogen Pressure vs. Dechlorination
with Calcined Platinum Catalyst 1 wt. % Pt/C

| # of Cycle | Hydrogen Pressure | 2-CA + 3-CA (mol. %) | 2-CA (mol. %) | 3-CA/2-CA ratio | Reaction time (min) |
|---|---|---|---|---|---|
| 19 | | — | — | — | 51 |
| 21 | | 0.16 | 0.050 | 2.18 | 52 |
| 27 | | 0.13 | 0.039 | 2.31 | 57 |
| 28 | | — | — | — | 57 |
| 33 | | — | — | — | — |
| 34 | 963 kPa | 0.11 | 0.031 | 2.66 | 48 |
| 35 | (125 psig) | — | — | — | 48 |
| 36 | | — | — | — | 48 |
| 37 | | — | — | — | 49 |
| 38 | | — | — | — | 49 |
| 39 | | — | — | — | 49 |
| 40 | | 0.081 | 0.022 | 2.72 | 50 |

The results show that higher hydrogen pressure accelerated the reaction to a degree. Also, increased hydrogen pressure slightly favored the dechlorination to 3-chloroaniline formation, as indicated by the increased ratio of 3-CA/2-CA.

Example 12: Platinum Leaching of Catalyst During Hydrogenation

Example 2 was repeated with a 1 wt. % Pt/C catalyst (without being calcined) and a 1 wt. % Pt/C catalyst that was calcined at 900° C. The 1 wt. % Pt/C catalyst was a commercial Pt/C catalyst. In these runs of the hydrogenation reaction procedure, approximately 755 mg (dry basis) of the catalyst and 150 g of a 30 wt. % 2,5-dichloronitrobenzene in acetic acid were loaded into the reactor. Hydrogen was charged to the reactor at a pressure of 687 kPa (85 psig). The reactor was heated to a temperature of 45° C. The reaction mixture at the end of hydrogenation cycles (cycle 1, 2, and 3) were evaluated for platinum leaching via a platinum metal analysis by an Inductively Coupled Plasma (ICP) method. The results of the platinum metal analyses are provided in Table 9.

TABLE 9

ICP Metal Analysis of Reaction Product Mixture
Leached Pt as a percentage of total Pt metal

| Catalyst Calcination | Hydrogenation Cycle 1 | Hydrogenation Cycle 2 | Hydrogenation Cycle 3 |
|---|---|---|---|
| none | 0.63 | 0.20 | 0.10 |
| 900° C. | 0.22 | 0.08 | 0.05 |

The calcination of the catalyst clearly decreased platinum leaching in the reaction environment.

Example 13: Performance of Catalysts Prepared by Various Methods

Example 2 was repeated with a variety of catalysts prepared by methods illustrated in Example 7 on activated carbon supports described in Example 10. The catalysts were either calcined at a high temperature (e.g., 800° C., 825° C., or 850° C.) or not calcined prior to use. In each run of the hydrogenation reaction procedure, approximately 755 mg (dry basis) of each catalyst and 150 g of a 30 wt. % 2,5-dichloronitrobenzene in acetic acid were loaded into the reactor. Hydrogen was charged to the reactor at a pressure of 687 kPa (85 psig). The reactor was heated to a temperature of 65° C. The results of these runs (average data of the first and second cycles) are provided in Table 10.

TABLE 10

Performance Summary of Catalysts Prepared by Various Methods

| | | | Catalyst Calcination | | | | |
|---|---|---|---|---|---|---|---|
| | | | None | | Calcined | | |
| Exp. No. | Method Number (Ex. 7) | Carbon Type (Ex. 10) | Reaction time (min) | 2-CA + 3-CA (mol. %) | Temperature (° C.) | Reaction time (min) | 2-CA + 3-CA (mol. %) |
| 13.1 | Ia | B | 39.7 | 0.52 | 850° C. | 49.5 | 0.25 |
| 13.2 | Ia[1] | B | 39.2 | 0.51 | 850° C. | 52.5 | 0.26 |
| 13.3 | Ia | A | 41.8 | 0.17 | 800° C. | 41.9 | 0.08 |
| 13.4 | II | B | 38.8 | 0.53 | 850° C. | 44.9 | 0.23 |
| 13.5 | III | B | 38.3 | 0.46 | 850° C. | 47.4 | 0.27 |
| 13.6 | IV | B | 37.3 | 0.50 | 850° C. | 47.5 | 0.21 |
| 13.7 | V | B | 37.7 | 0.52 | 850° C. | 44.9 | 0.27 |
| 13.8 | VI | B | 39.8 | 0.54 | 850° C. | 52.0 | 0.26 |
| 13.9 | VI | B | 39.8 | 0.54 | 850° C.[3] | 69.4 | 0.27 |
| 13.10 | VII | B | 42.9 | 0.43 | 850° C. | 48.0 | 0.29 |
| 13.11 | VIIIb | B | 35.8 | 0.53 | 850° C. | 67.3 | 0.24 |
| 13.12 | IX | B | 38.8 | 0.54 | 825° C. | 61.2 | 0.24 |
| 13.13 | Xa | B | 35.9 | 0.62 | 850° C. | 43.9 | 0.30 |
| 13.14 | Xb | B | 33.7 | 0.60 | 850° C. | 42.8 | 0.29 |
| 13.15 | Ib[2] | B | 62.3 | 0.44 | 800° C. | 69.9 | 0.16 |
| 13.16 | Ib[2] | B | 62.3 | 0.44 | 850° C.[3] | 154.5 | 0.26 |
| 13.17 | Ib[2] | B | 62.3 | 0.44 | 750° C.[3] | 42.4 | 0.66 |

[1]The initial pH of Method Ia was adjusted to pH 8.47;
[2]No NaBH$_4$ reduction;
[3]Calcination in the presence of 5% hydrogen gas.

The selectivity loss to 2- and 3-chloroaniline upon dechlorination of 2,5-dichloroaniline is dependent on the nature and the porosity of the activated carbon support. The catalyst prepared on carbon type A appeared to provide less dichlorinated products.

There is no significant difference of dechlorination selectivity observed with catalysts prepared by various parameters such as pHs and temperatures on the same type of activated carbon (e.g., Method Ia, II, III, IV, V, VI, and VII).

A slightly increased dechlorination to 2- and 3-chloroaniline was observed with the catalysts prepared by Method Xa and Xb, where the pH of the chloroplatinic acid solution was pre-adjusted to higher pHs (e.g., about pH 11).

Figure 14:
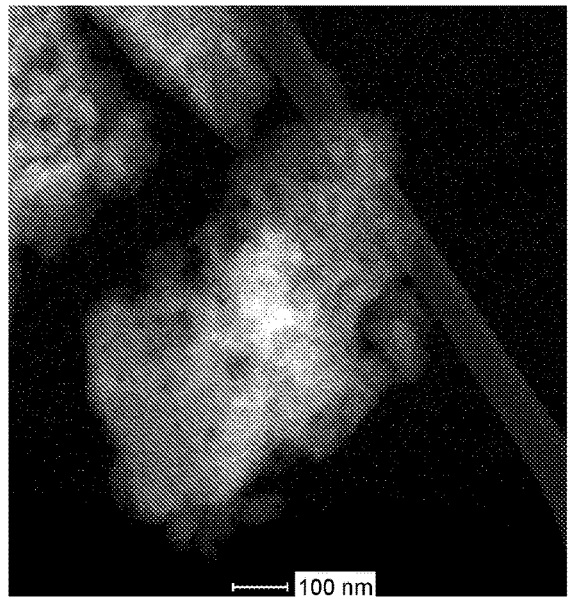
FIG. 14 presents a series of STEM images of the surface of an un-reduced plantinum precursor on carbon catalyst after calcination in the presence of 5% hydrogen gas.
Figure 14:
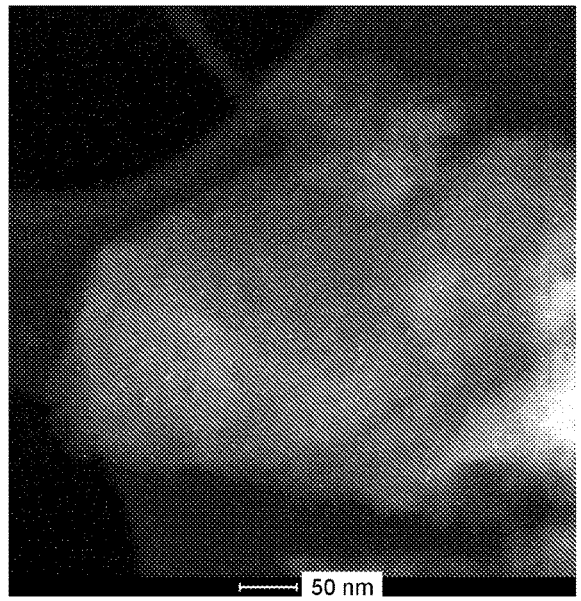
Figure 14:
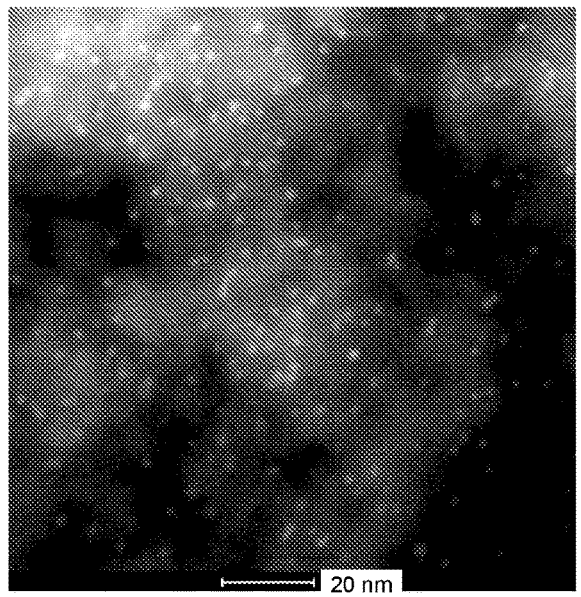
Figure 15:
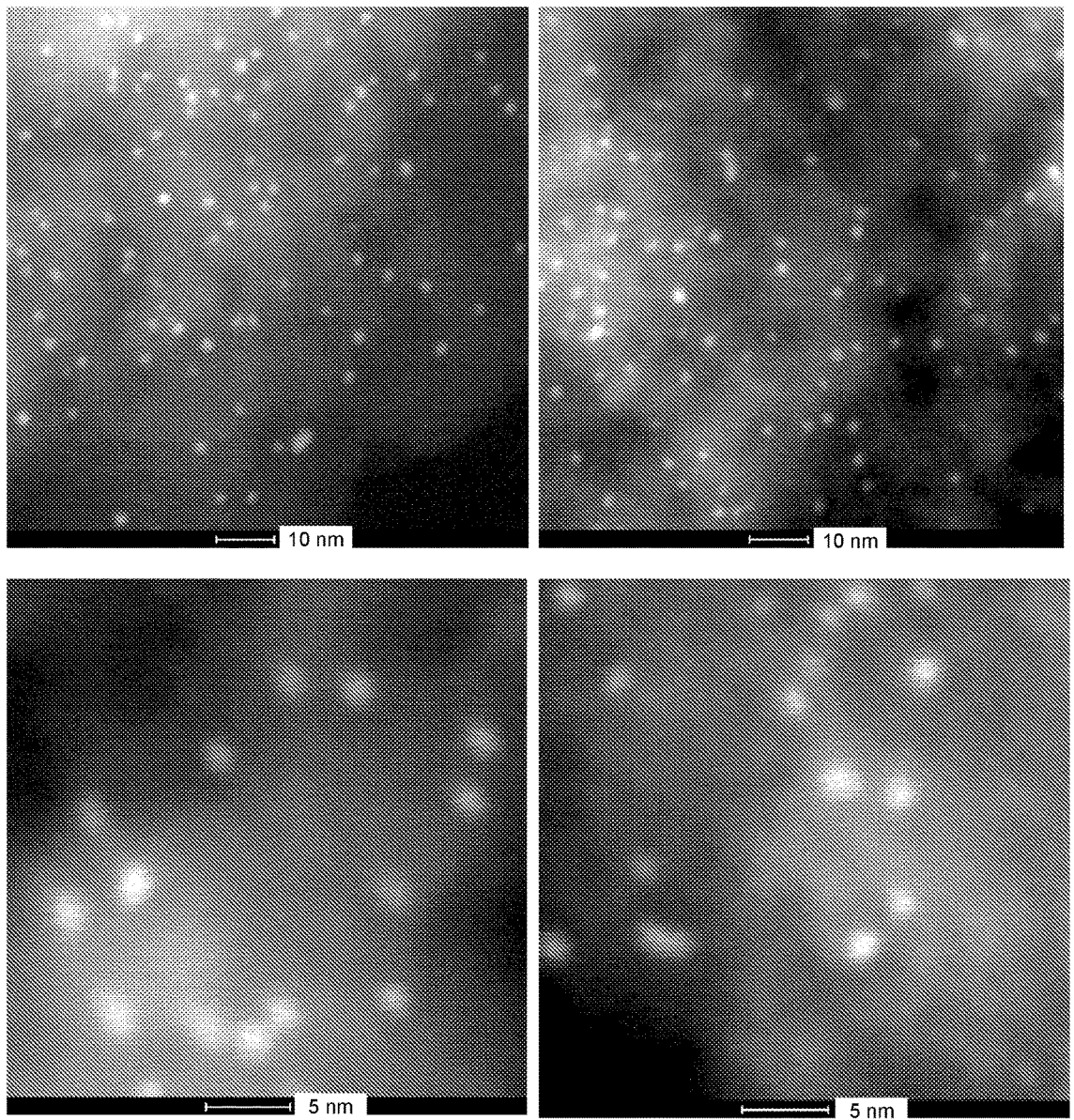
FIG. 15 presents a series of STEM images of the surface of an un-reduced plantinum precursor on carbon catalyst after calcination in the presence of 5% hydrogen gas.

A better dechlorination selectivity was achieved with the catalyst prepared by Method Ib, where the plantinum precursor was not reduced. However, the activity of the catalyst was observed to be less, as represented as having longer reaction time. The lower activity with improved selectivity were attributed to the excessive agglomeration of the platinum, which was in-situ reduced by the hydrogen during the hydrogenation reaction, resulting in an excessive Ostwald ripening type plantinum movement. A better approach is to calcine the un-reduced plantinum precursor on carbon in an inert atmosphere at a high-temperature. Since metal oxides in general have higher mobility on support surface, the high-temperature calcination of an un-reduced plantinum precursor in an inert atmosphere will lead to more platinum agglomeration before the platinum is reduced at a high temperature (e.g., 800° C.) by the carbon. This is consistent with the results of observed good dechlorination selectivity (i.e., 0.16 mol %) but with longer reaction time (i.e., 69.9 minutes).

leads to platinum agglomeration after calcinations of the un-reduced plantinum precursor on carbon at a high temperature (e.g., 800° C.). The catalyst surface from Experiment 13.17 was also imaged after calcination (in the presence of 5% hydrogen gas at 750° C.) using STEM. FIGS. 14 and 15 present a series of images for the catalyst surface after calcinations in the presence of 5% hydrogen gas at 750° C. These images show that the high-temperature treatment of catalysts under hydrogen atmosphere reduces platinum agglomeration of the un-reduced plantinum precursor on carbon.

Example 15: Hydrogenation Parameters in Various Reaction Solvents

Example 2 was repeated with a catalyst prepared by Method V of Example 7 on activated carbon (type-B of Example 10), which was used as-synthesized without being calcined; and the reaction solvent was varied between runs. In these runs of the hydrogenation reaction procedure, approximately 755 mg (dry basis) of the catalyst and 150 g of a 30 wt. % 2,5-dichloronitrobenzene in a solvent (i.e., acetic acid, isopropanol, or methanol) were loaded into the reactor. The amount of hydrogen charged to the reactor was 687 kPa (85 psig) for runs in either acetic acid or isopropanol, and 584 kPa (70 psig) for runs in methanol. The temperature of the reactor was varied at 65° C. (for runs in acetic acid or isopropanol), 55° C. (for runs in isopropanol), or 45° C. (for runs in methanol). The results of these runs after nine reaction cycles are provided in Table 11.

TABLE 11

Reaction Parameters in Various Solvents

| | Acetic Acid (85 psig H$_2$, 65° C.) | | Isopropanol (85 psig H$_2$, 65° C.) | | Isopropanol (85 psig H$_2$, 55° C.) | | Methanol (70 psig H$_2$, 45° C.) | |
|---|---|---|---|---|---|---|---|---|
| Cycle # | 2-CA + 3-CA (mol. %) | Reaction time (min) | 2-CA + 3-CA (mol. %) | Reaction time (min) | 2-CA + 3-CA (mol. %) | Reaction time (min) | 2-CA + 3-CA (mol. %) | Reaction time (min) |
| 1 | 0.54 | 39.7 | 0.50 | 40.8 | 0.39 | 41.8 | 0.58 | 39.7 |
| 2 | 0.63 | 36.7 | 0.62 | 36.7 | 0.56 | 39.8 | 0.65 | 34.6 |
| 3 | 0.63 | 39.9 | 0.82 | 36.8 | 0.62 | 40.8 | 0.57 | 39.7 |
| 4 | 0.58 | 35.6 | 0.93 | 37.7 | 0.39 | 38.7 | — | — |
| 5 | 0.62 | 36.6 | 0.89 | 35.7 | 0.54 | 38.6 | 0.51 | 40.8 |
| 6 | 0.56 | 35.7 | 0.83 | 36.7 | 0.64 | 40.9 | 0.50 | 46.0 |
| 7 | 0.49 | 35.7 | 0.47 | 34.7 | 0.59 | 40.8 | 0.48 | 42.8 |
| 8 | 0.53 | 36.7 | 0.72 | 34.7 | 0.40 | 38.8 | 0.48 | 41.8 |
| 9 | 0.56 | 35.7 | 0.80 | 35.7 | 0.49 | 38.7 | 0.48 | 42.8 |
| Average | 0.57 | 36.9 | 0.73 | 36.6 | 0.51 | 39.9 | 0.53 | 41.0 |

In general, high-temperature treatment of catalysts under hydrogen atmosphere reduced the catalyst activity due to possible spillover of carbonaceous materials over the platinum surface.

Example 14: Performance of Catalysts Prepared by Various Methods

Figure 10:
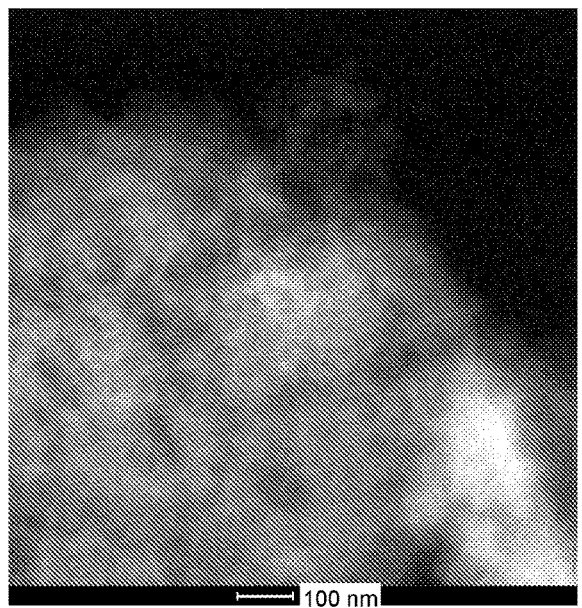
FIG. 10 presents a series of STEM images of the surface of an un-reduced plantinum precursor on carbon catalyst before calcination.
Figure 10:
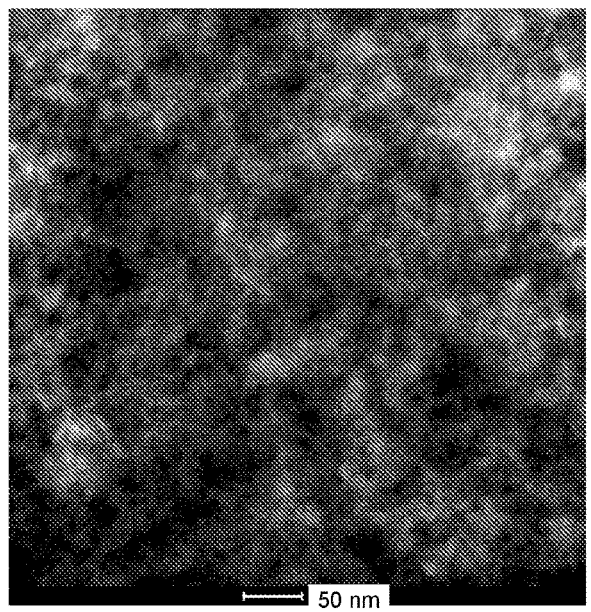
Figure 10:
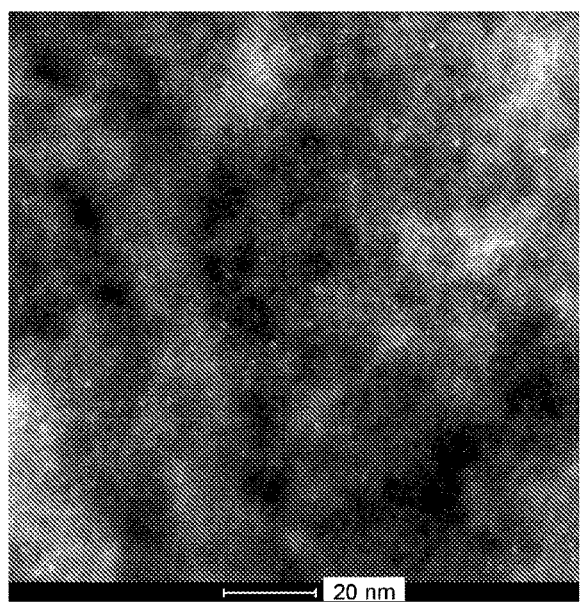
Figure 10:
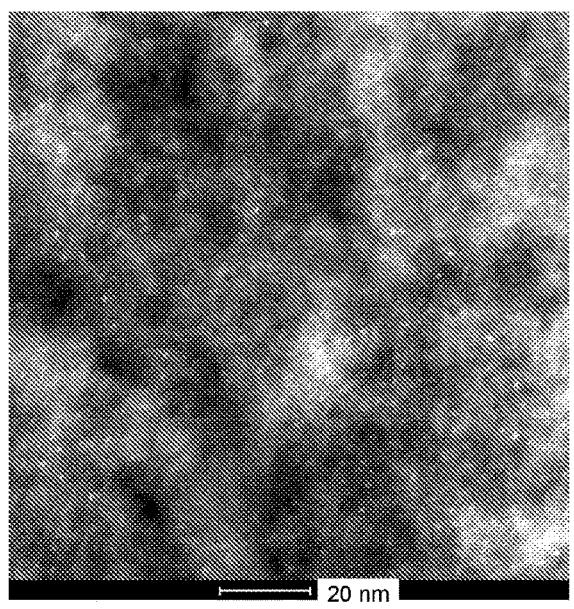
Figure 11:
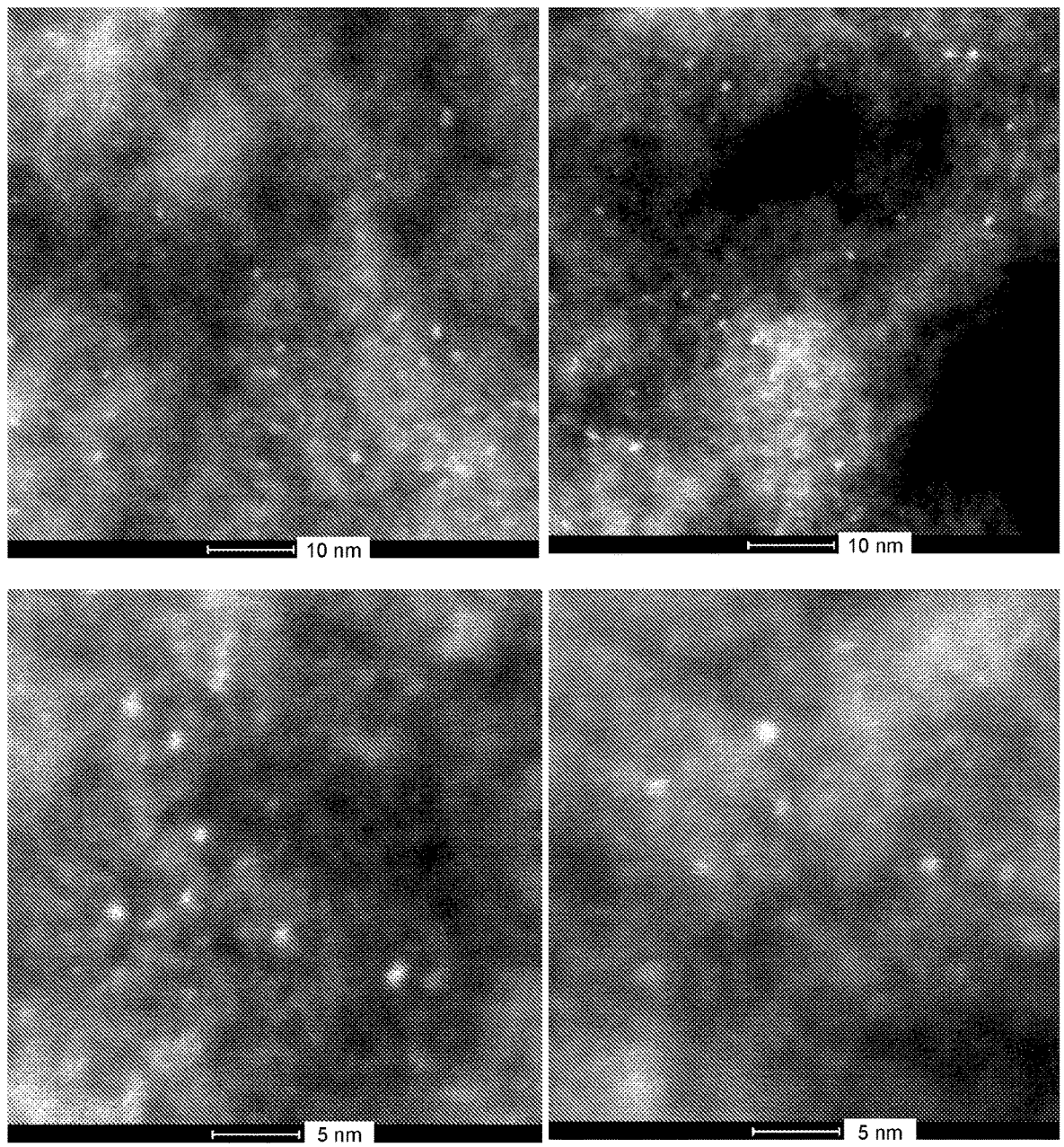
FIG. 11 presents a series of STEM images of the surface of an un-reduced plantinum precursor on carbon catalyst before calcination.
Figure 12:
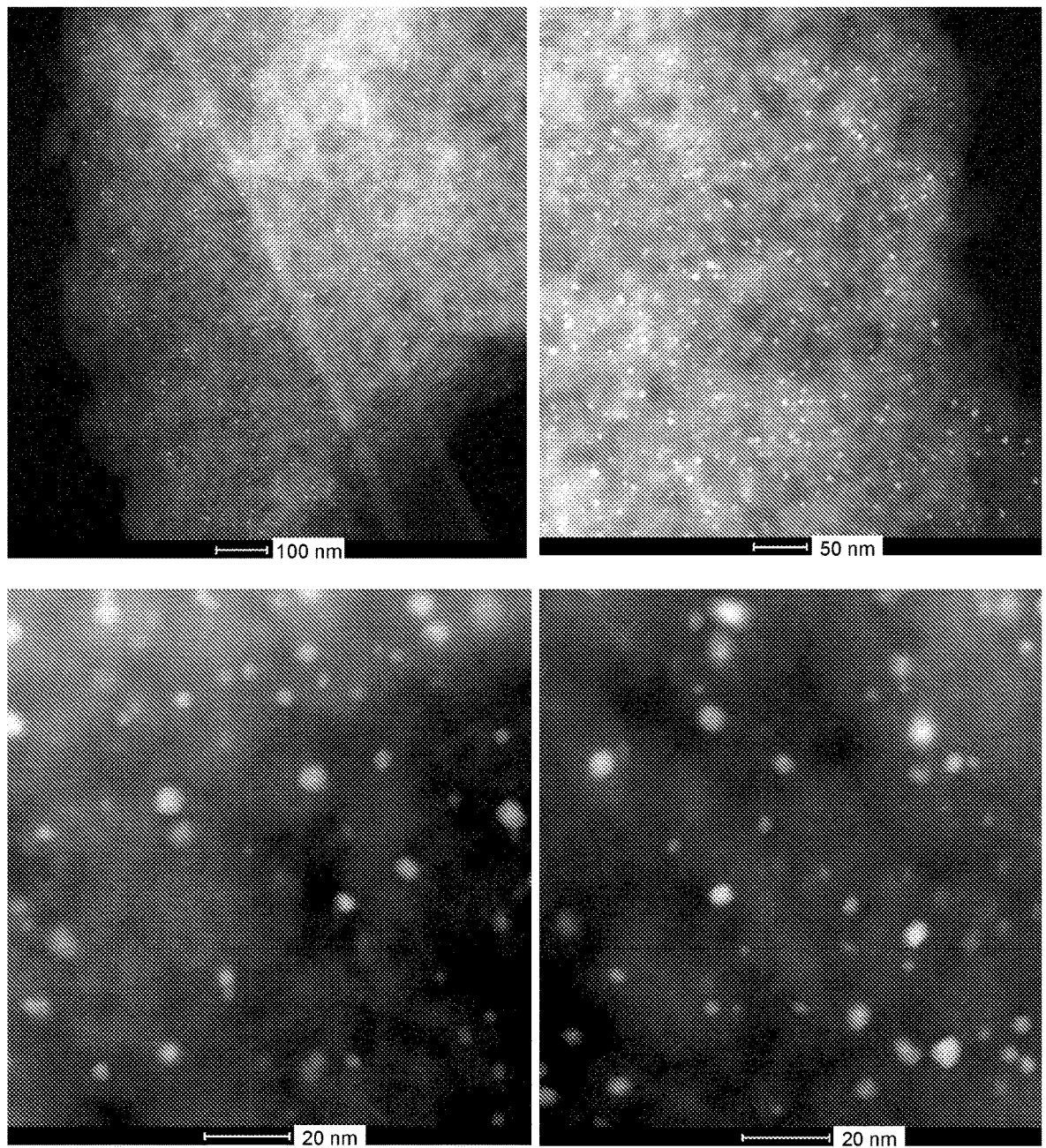
FIG. 12 presents a series of STEM images of the surface of an un-reduced plantinum precursor on carbon catalyst after calcination.
Figure 13:
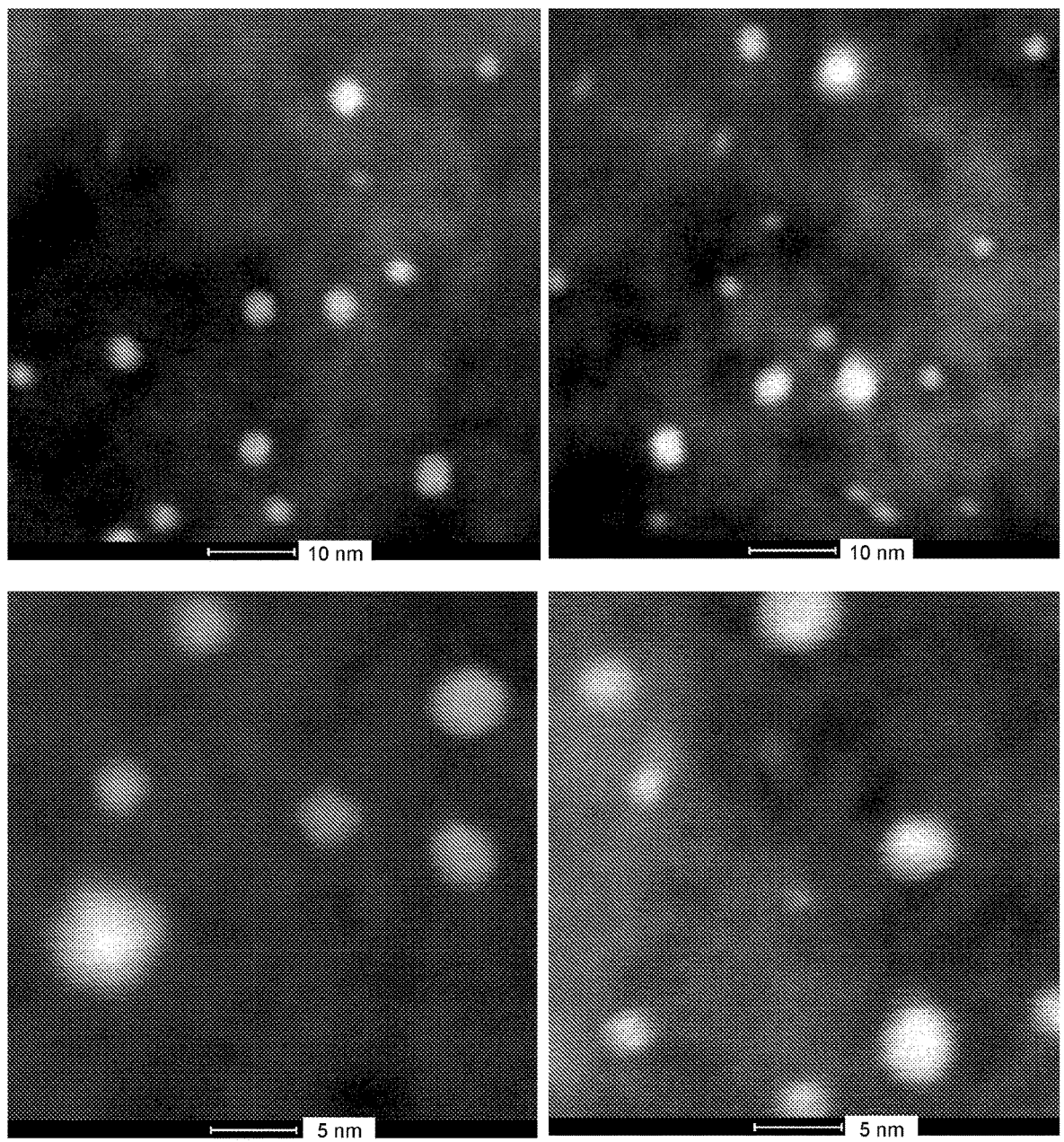
FIG. 13 presents a series of STEM images of the surface of an un-reduced plantinum precursor on carbon catalyst after calcination.

The catalyst surface from Exp. 13.15 (i.e., the catalyst was prepared without NaBH$_4$ reduction) of Example 13 was imaged before calcination and after calcination (at 800° C.) using STEM. FIGS. 10 and 11 present a series of images for the catalyst surface before calcination. FIGS. 12 and 13 present a series of images for the catalyst surface after calcination at 800° C. These images show that the catalyst In order to have a similar performance of the catalyst in acetic acid, the reaction parameters (i.e., reaction temperature and hydrogen pressure) were adjusted for runs in either isopropanol or methanol. The dechlorination to 2- and 3-chloroaniline in either isopropanol (at 55° C., 85 psig H$_2$) or methanol (45° C., 70 psig H$_2$) is similar to the one in acetic acid (65° C., 85 psig H$_2$), illustrated in Table 11. The average reaction time were similar under all conditions, as of 36.9, 36.6, 39.9 and 41.0 minutes for acetic acid (at 65° C., 85 psig H$_2$), isopropanol (at 65° C., 85 psig H$_2$), isopropanol (at 55° C., 85 psig H$_2$), and methanol (at 45° C., 70 psig H$_2$); respectively.

When introducing elements of the present invention or the preferred embodiments(s) thereof, the articles "a", "an", "the" and "said" are intended to mean that there are one or

What is claimed is:

1. A process for producing 2,5-dichloroaniline, the process comprising:
   feeding hydrogen and a feed mixture comprising 2,5-dichloronitrobenzene and a solvent comprising water, alcohol, and/or an acid to a hydrogenation zone; and
   reacting the 2,5-dichloronitrobenzene with hydrogen in the presence of a heterogeneous hydrogenation catalyst comprising platinum on a carbon support to produce a reaction product comprising 2,5-dichloroaniline,
   wherein the hydrogenation catalyst has a platinum loading that is from about 0.1 wt. % to about 1.5 wt. % and has been calcined at a temperature of from about 500° C. to about 1000° C.

2. The process of claim 1 wherein the feed mixture is free of dehalogenation suppressors.

3. The process of claim 1 wherein the hydrogenation catalyst has a platinum loading that is from about 0.5 wt. % to about 1.5 wt. %.

4. The process of claim 1 wherein the hydrogenation catalyst is prepared by heating the carbon support having platinum thereon to a temperature of from about 700° C. to about 1000° C.

5. The process of claim 1 wherein the hydrogenation catalyst is prepared by heating the carbon support having platinum thereon to a temperature of from about 800° C. to about 950° C.

6. The process of claim 1 wherein the hydrogenation catalyst comprises unreduced platinum.

7. The process of claim 6 wherein the hydrogenation catalyst is prepared by depositing the platinum onto the carbon support without use of a reducing agent; and calcining the platinum on the carbon support.

8. The process of claim 1 wherein the carbon support is a particulate.

9. The process of claim 1 wherein the hydrogenation catalyst comprises platinum metal particles at the surface of the carbon support of a size up to 10 nm in their largest dimension and at least about 25% (number basis) of the platinum metal particles are from 2 nm to 10 nm in their largest dimension.

10. The process of claim 1 wherein the hydrogenation catalyst comprises platinum metal particles of a size up to 10 nm in their largest dimension and these particles are characterized as having an average particle size from about 2.5 to about 8 nm.

11. The process of claim 1 wherein the hydrogenation catalyst comprises platinum metal particles of a size up to 10 nm in their largest dimension and no more than about 50% (number basis) of the platinum metal particles are less than 2 nm in their largest dimension.

12. The process of claim 1 wherein the hydrogenation catalyst is essentially free of metal catalyst modifiers.

13. The process of claim 1 wherein the carbon support has a total Langmuir specific surface area that is from about 500 m²/g to about 3000 m²/g.

14. The process of claim 1 wherein the carbon support has a Langmuir micropore surface area that is from about 750 m²/g to about 2000 m²/g.

15. The process of claim 1 wherein the carbon support has an average pore diameter that is in the range of from about 0.5 nm to about 5 nm.

16. The process of claim 1 wherein the carbon support has a pore volume of at least about 0.3 ml/g.

17. The process of claim 1 wherein the carbon support of the hydrogenation catalyst comprises activated carbon.

18. The process of claim 1 wherein the hydrogenation catalyst that is introduced into the hydrogenation zone consists essentially of platinum on a carbon support.

19. The process of claim 1 wherein the hydrogenation catalyst is essentially free of alkali and alkali earth metals.

20. The process of claim 1 wherein the solvent comprises the acid.

21. The process of claim 20 wherein the acid comprises an organic acid selected from the group consisting of formic acid, acetic acid, propionic acid, butyric acid, citric acid, and mixtures thereof.

22. The process of claim 1 wherein the solvent is from about 20 wt. % to about 95 wt. % of the feed mixture.

23. The process of claim 1 wherein the hydrogenation reaction is conducted at a temperature that is from about 20° C. to about 100° C.

24. The process of claim 1 wherein hydrogenation reaction is conducted under a partial pressure of hydrogen that is at least about 20 kPa.

25. The process of claim 1 wherein the feed mixture is free or essentially free of hydroxides or oxides of magnesium, cycloaliphatic amines, and acidic phosphorous compounds.

26. The process of claim 1 wherein the reaction product further comprises 2-chloroaniline and 3-chloroaniline.

27. The process of claim 26 wherein the mole ratio of 3-chloroaniline to 2-chloroaniline is no greater than about 6:1.

28. The process of claim 1 wherein the yield of 2,5-dichloroaniline is at least about 90%.

29. The process of claim 1 wherein the reaction product further comprises platinum and the process further comprises recovering platinum from the reaction product.

30. A process for preparing 3,6-dichloro-2-methoxybenzoic acid or salt or ester thereof, the process comprising:
   producing 2,5-dichloroaniline according to claim 1;
   diazotizing 2,5-dichloroaniline to provide 2,5-dichlorobenzenediazonium;
   hydrolyzing 2,5-dichlorobenzenediazonium to form 2,5-dichlorophenol;
   carboxylating 2,5-dichlorophenol to form 2-hydroxy-3,6-dichlorobenzoic acid;
   methylating 2-hydroxy-3,6-dichlorobenzoic acid to form a methylation reaction product comprising 3,6-dichloro-2-methoxybenzoic acid salt and/or ester thereof; and
   optionally saponifiying the methylation reaction product to form 3,6-dichloro-2-methoxybenzoic acid.

31. The process of claim 26 wherein the mole ratio of 3-chloroaniline to 2-chloroaniline is from about 1:1 to about 5:1.

32. The process of claim 26 wherein the loss of selectivity from 2,5-dichloroaniline to 2-chloroaniline and 3-chloroaniline is less than about 0.4 mol.%.

33. The process of claim 1 wherein the solvent comprises the alcohol.

34. The process of claim 33 wherein the alcohol is selected from the group consisting of methanol, ethanol, propanol, isopropanol, 1-butanol, 2-butanol, t-butanol, and mixtures thereof.

* * * * *